United States Patent
Garrison et al.

[11] Patent Number: 5,972,030
[45] Date of Patent: Oct. 26, 1999

[54] LESS-INVASIVE DEVICES AND METHODS FOR TREATMENT OF CARDIAC VALVES

[75] Inventors: Michi E. Garrison, Belmont; Brian S. Donlon, Los Altos Hills; S. Christopher Daniel, San Francisco, all of Calif.; John H. Stevens, London, United Kingdom

[73] Assignee: Heartport, Inc., Redwood City, Calif.

[21] Appl. No.: 08/949,282

[22] Filed: Oct. 21, 1997

Related U.S. Application Data

[63] Continuation of application No. 08/485,600, Jun. 7, 1995, abandoned, which is a continuation-in-part of application No. 08/281,962, Jul. 28, 1994, abandoned, which is a continuation-in-part of application No. 08/163,241, Dec. 6, 1993, Pat. No. 5,571,215, which is a continuation-in-part of application No. 08/023,778, Feb. 22, 1993, Pat. No. 5,452,733.

[51] Int. Cl.⁶ ..................................................... A61F 2/24
[52] U.S. Cl. ..................................................... 623/2
[58] Field of Search ................................ 606/205, 206, 606/151, 159, 148, 150, 1; 623/2, 66

[56] References Cited

U.S. PATENT DOCUMENTS

| | | | |
|---|---|---|---|
| 3,409,013 | 11/1968 | Berry .......................................... | 623/2 |
| 4,042,979 | 8/1977 | Angell . | |
| 4,056,854 | 11/1977 | Boretos et al. . | |
| 4,173,981 | 11/1979 | Mortensen .............................. | 128/348 |
| 4,217,665 | 8/1980 | Bex et al. . | |
| 4,489,446 | 12/1984 | Reed . | |
| 4,602,911 | 7/1986 | Ahmadi et al. . | |
| 4,655,218 | 4/1987 | Kulik et al. . | |
| 4,679,556 | 7/1987 | Lubock et al. . | |
| 4,917,698 | 4/1990 | Carpentier et al. ......................... | 623/2 |
| 4,960,424 | 10/1990 | Grooters . | |
| 5,011,481 | 4/1991 | Myers et al. . | |
| 5,032,128 | 7/1991 | Alonso . | |
| 5,041,130 | 8/1991 | Cosgrove et al. . | |
| 5,061,277 | 10/1991 | Carpentier et al. . | |
| 5,064,431 | 11/1991 | Gilbertson et al. . | |

(List continued on next page.)

FOREIGN PATENT DOCUMENTS

| | | |
|---|---|---|
| 0 218 275 | 4/1987 | European Pat. Off. . |
| 2681775 | 4/1993 | France . |
| WO 87/05489 | 9/1987 | WIPO . |
| WO 93/20742 | 10/1993 | WIPO . |

OTHER PUBLICATIONS

Berreklouw et al. "Revival of Right Thoracotomy to Approach to Atrio-ventricular Valves in Reoperations" *Thorac Cardiovasc Surgeon* (1984) 32:331–333.

(List continued on next page.)

*Primary Examiner*—David J. Isabella
*Attorney, Agent, or Firm*—Jens E. Hoekendijk; Jeffry J. Grainger

[57] ABSTRACT

Devices and methods are provided for less-invasive surgical treatment of cardiac valves whereby the need for a gross thoracotomy or median sternotomy is eliminated. In one aspect of the invention, a delivery system for a cardiac valve prosthesis such as an annuloplasty ring or prosthetic valve includes an elongated handle configured to extend into the heart through an intercostal space from outside of the chest cavity, and a prosthesis holder attached to the handle for releasably holding a prosthesis. The prosthesis holder is attached to the handle in such a way that the holder, prosthesis and handle have a profile with a height smaller than the width of an intercostal space when the adjacent ribs are unretracted, preferably less than about 30 mm. In a further aspect, the invention provides a method for repairing or replacing a heart valve which includes the steps of introducing a prosthesis through an intercostal space and through a penetration in a wall of the heart, and securing the prosthesis to an interior wall of the heart, wherein each step is carried out without cutting, removing, or significantly retracting the ribs or sternum.

30 Claims, 27 Drawing Sheets

U.S. PATENT DOCUMENTS

| | | |
|---|---|---|
| 5,104,407 | 4/1992 | Lam et al. . |
| 5,109,859 | 5/1992 | Jenkins ..................................... 128/662 |
| 5,188,619 | 2/1993 | Myers ...................................... 604/280 |
| 5,197,979 | 3/1993 | Quintero et al. . |
| 5,201,880 | 4/1993 | Wright et al. . |
| 5,203,776 | 4/1993 | Durfee ..................................... 604/264 |
| 5,250,038 | 10/1993 | Melker et al. ........................... 604/264 |
| 5,258,021 | 11/1993 | Duran . |
| 5,271,385 | 12/1993 | Bailey . |
| 5,290,300 | 3/1994 | Cosgrove et al. ........................... 623/2 |
| 5,304,187 | 4/1994 | Green et al. ............................. 606/151 |
| 5,306,296 | 4/1994 | Wright et al. . |
| 5,308,320 | 5/1994 | Safar et al. ................................. 604/4 |
| 5,332,402 | 7/1994 | Teitelbaum ................................. 623/2 |
| 5,350,420 | 9/1994 | Cosgrove et al. . |
| 5,376,112 | 12/1994 | Duran . |
| 5,383,888 | 1/1995 | Zvenyatsky et al. .................... 606/206 |
| 5,391,156 | 2/1995 | Hildwein et al. ....................... 606/174 |
| 5,403,305 | 4/1995 | Sauter et al. . |
| 5,490,843 | 2/1996 | Hildwein et al. ....................... 604/164 |
| 5,560,487 | 10/1996 | Starr . |
| 5,578,076 | 11/1996 | Krueger et al. . |

OTHER PUBLICATIONS

Buckberg, G.D. "Strategies and logic of cardioplegic delivery to prevent, avoid, and reverse ischemic and reperfusion damage" *J. Thorac Cardiovasc Surg.* (1987) 93:127–139.

Yamaguchi et al. "A case of a reoperation using a balloon catheter with blocked pars acendes aortae" *Kyobu Geka,* (1991) 42(11):961–964.

Meditech®, Instructions for Use, Occlusion Balloon Catheters Rev. Mar. 1991, pp. 1–7.

Peters, W.S. "Minimally invasive cardiac surgery by cardioscopy" *AustralAs J. Cardiac Thorac Surg.* (1993) 2(3):152–154.

Cosgrove, D.M. "Management of the Calcified Aorta: An Alternative Method of Occlusion" *Ann Thorac Surg.* (1983) 36:718–719.

J.H. Foster and J.B. Threlkel "Proximal Control of Aorta with a Balloon Catheter" *Surg, Gynecology & Obstetrics* (1971) pp. 693–694.

H.G. Erath, Jr. and William S. Stoney, Jr. "Balloon Catheter Occlusion of the Ascending Aorta" *Ann Thorac Surg.* (1983) 35:560–561.

Sakaguchi et al. "Aortic Valve Replacement and Coronary Artery Bypass" *J. Japanese Assoc. for Thoracic Surgery* (1993) 41(6):1063–1068.

Coltharp, William H., et al. "Videothorascopy . . . " *Ann Thorac Surg* (1992) 53:776–9.

Jamieson, W.R. Eric "Modern Cardiac Valve Devices–Bioprostheses and Mechanical Prostheses" *J Card Surg* (1993) 8:89–98.

Landreneau et al., "Video–Assisted Thoracic Surgery . . . " *Ann Thorac Surg* (1992) 54:800–7.

Mack et al. "Present Role of Thoracoscopy in the Diagnosis and Treatment of Diseases of the Chest" *Ann Thorac Surg* (1992) 54:403–9.

Magovern, George J. "Sutureless Aortic and Mitral Prosthetic Valves" *J Thoracic and Cardiovasc Surg* (1964) 48(3):346–361.

Ozuner et al. "Creation of a Pericardial Window Using Thoracoscopic Techniques" *Surg. Gynecology & Obstetrics* (1992) 175:69–71.

Wakabayashi, Akio "Expanded Applications of Diagnostic and Therapeutic Thoracoscopy" *J Thorac and Cardiovasc Surg* (1991) 102:721–3.

Cohn et al. "Right Thoracotomy, Femorofemoral Bypass, and Deep Hypothermia for Re–replacement of the Mitral Valve" *Ann Thorac Surg* (1989) 48:69–71.

Fundaro et al. "Towards an easier and safer reoperation of the atrioventricular valves. The right anterolateral thoracotomy approach without pericardial dissection" *J. Cardiovasc Surg* (1989) 30:779–781.

Tribble et al. "Anterolateral Thoracotomy as an Alternative to Repeat Median Sternotomy for Replacement of the Mitral Valve" *Ann Thorac Surg* (1987) 43:380–382.

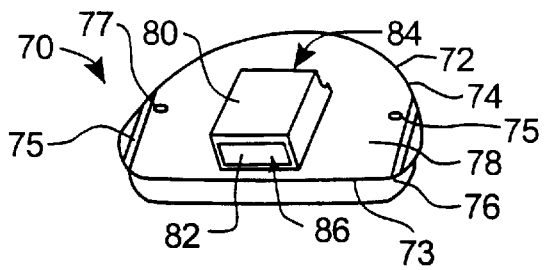
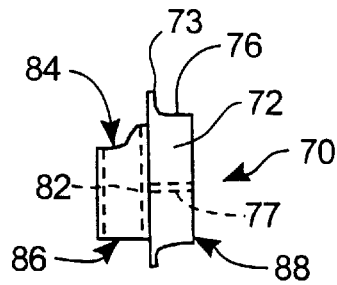
FIG. 5A
FIG. 5C
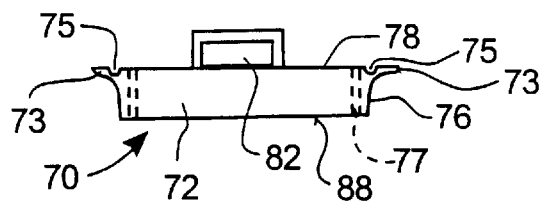
FIG. 5B
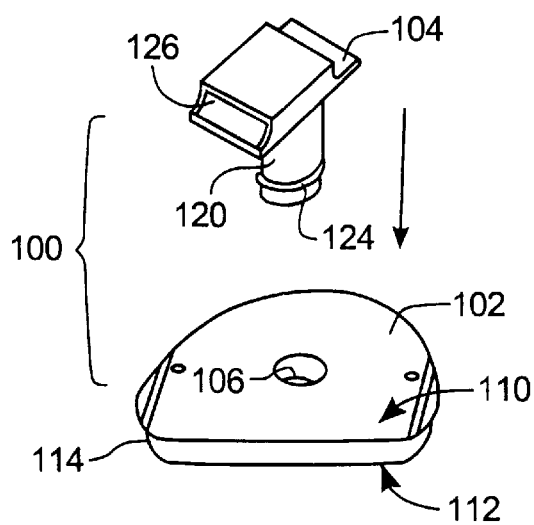
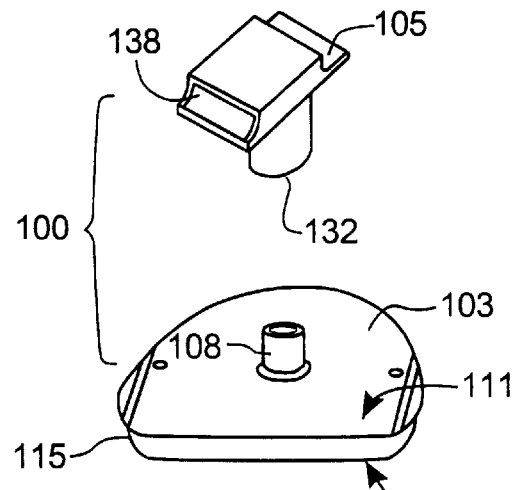
FIG. 12A
FIG. 12B

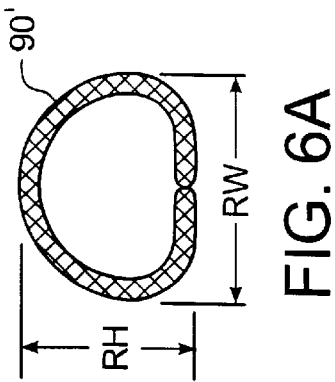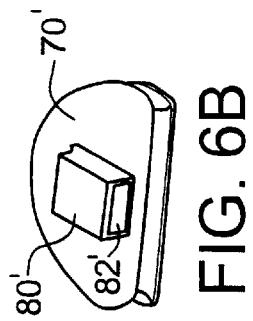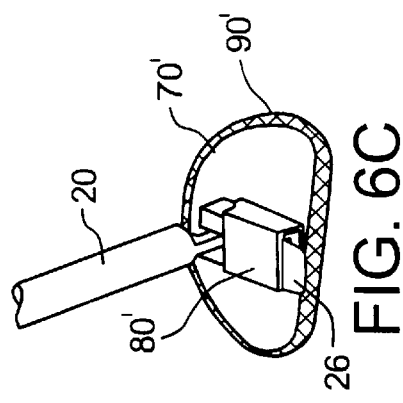
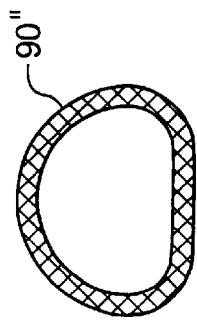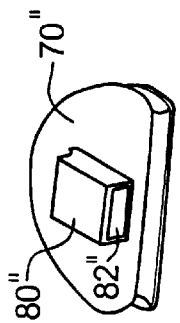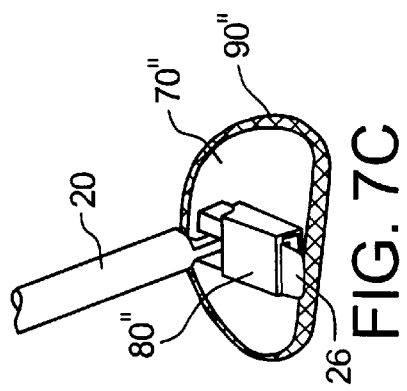
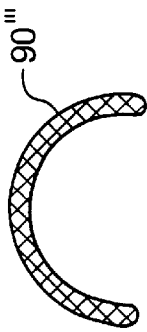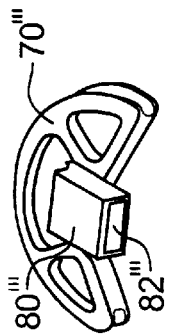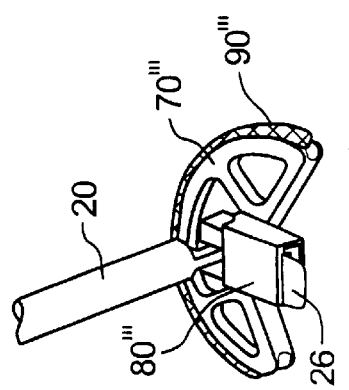

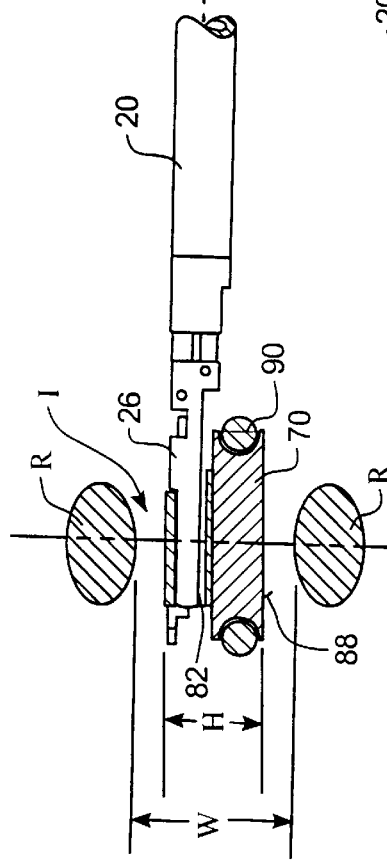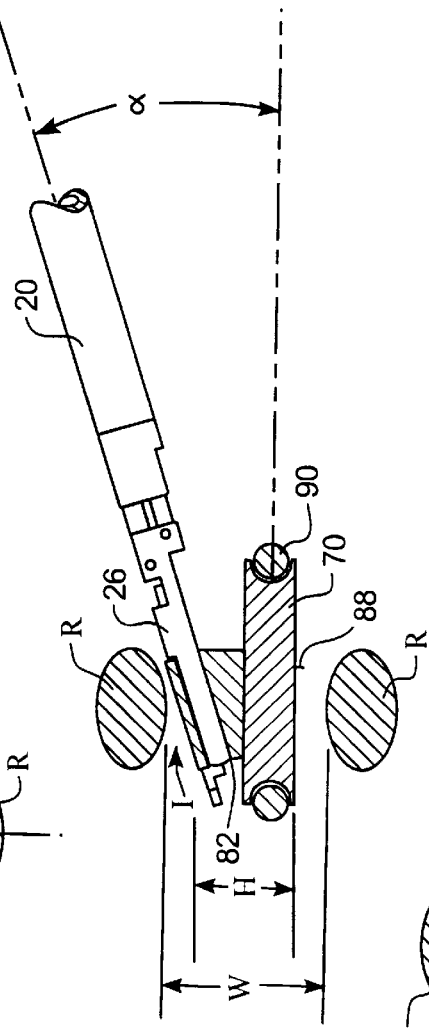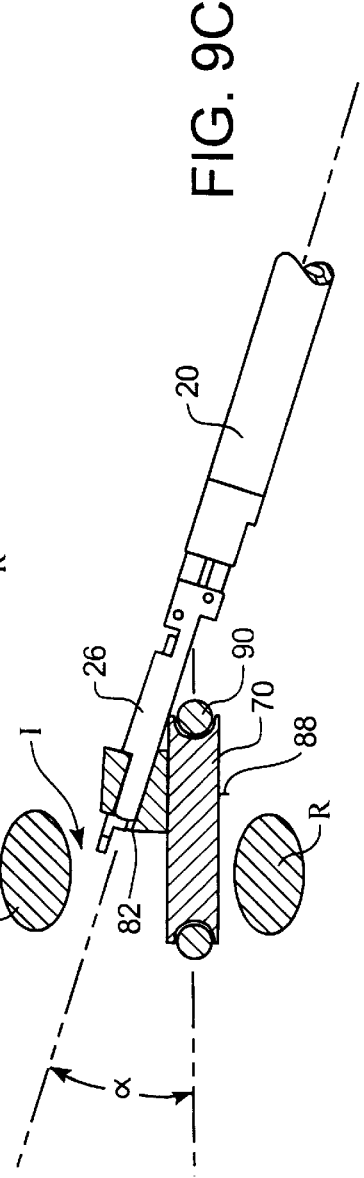

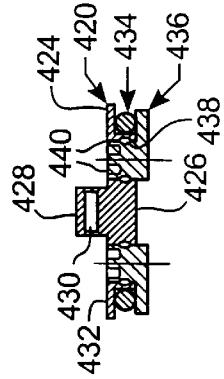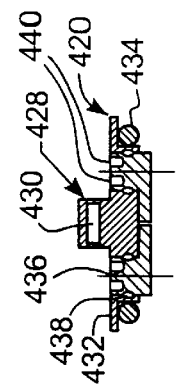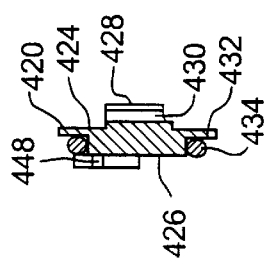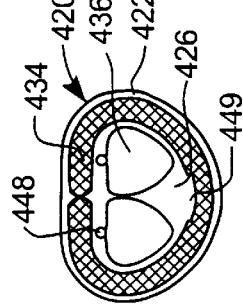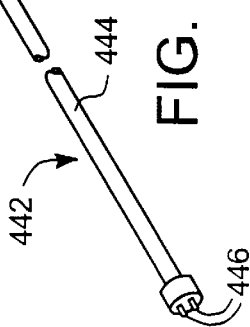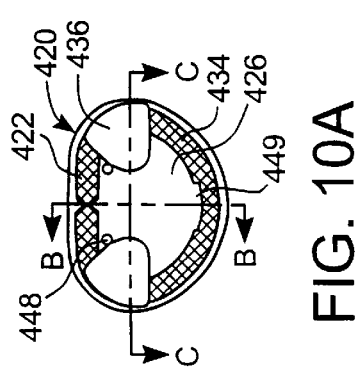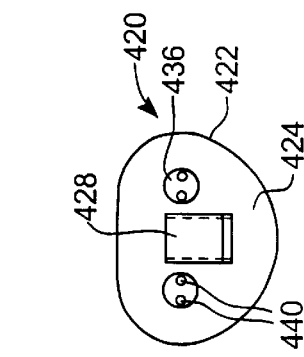

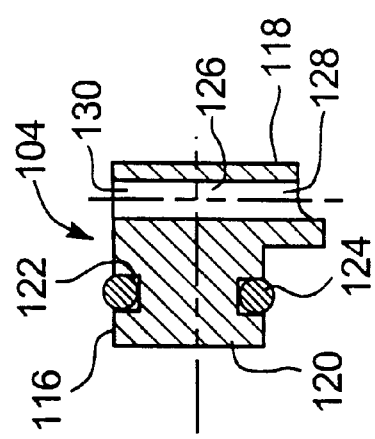
FIG. 13C
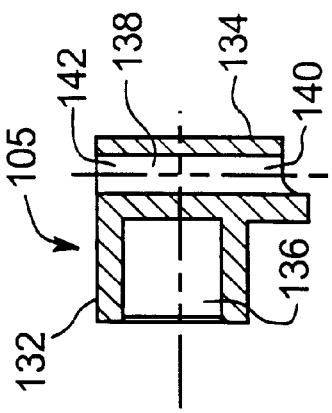
FIG. 14C
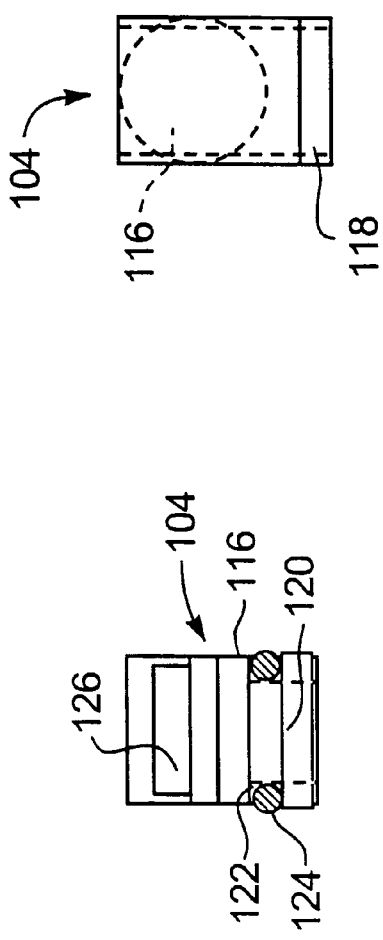
FIG. 13B
FIG. 13A
FIG. 14B
FIG. 14A

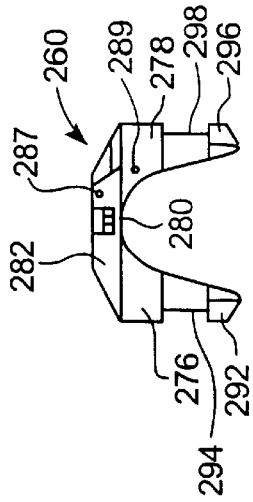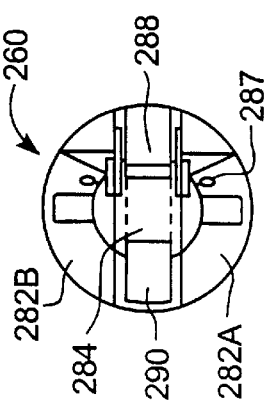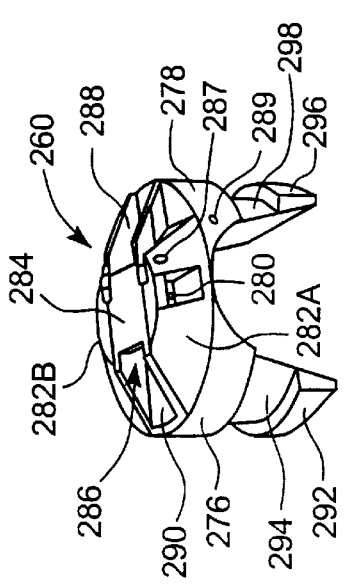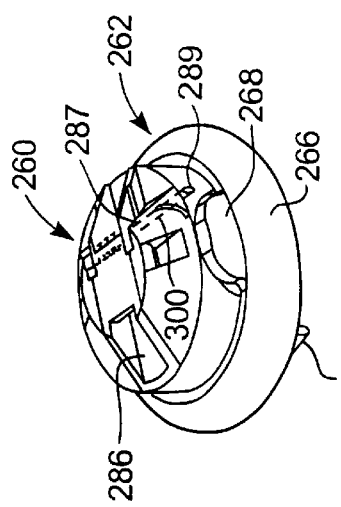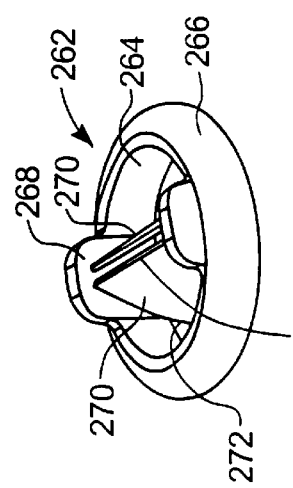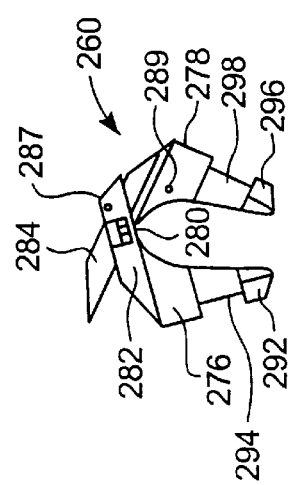

LESS-INVASIVE DEVICES AND METHODS FOR TREATMENT OF CARDIAC VALVES

CROSS-REFERENCE TO RELATED APPLICATIONS

This application is a Continuation of Ser. No. 08/485,600, filed Jun. 7, 1995, now abandoned, which was a Continuation-In-Part of application Ser. No. 08/281,962, filed Jul. 28, 1994, now abandoned, which is a Continuation-In-Part of application Ser. No. 08/163,241, filed Dec. 6, 1993, now U.S. Pat. No. 5,571,215, which is a Continuation-In-Part of application Ser. No. 08/023,778, filed Feb. 22, 1993, now U.S. Pat. No. 5,452,733, the complete disclosures of which are hereby incorporated herein by reference for all purposes.

FIELD OF THE INVENTION

The present invention relates generally to devices and methods for performing surgery on the heart. More specifically, the invention relates to less-invasive devices and methods for the surgical treatment of diseased heart valves.

BACKGROUND OF THE INVENTION

Heart valve disease is a widespread condition in which one or more of the valves of the heart fails to function properly. Diseased heart valves may be categorized as either stenotic, wherein the valve does not open sufficiently to allow adequate forward flow of blood through the valve, or incompetent, wherein the valve does not close completely, causing excessive backward flow of blood through the valve when the valve is closed. A heart valve may also be both stenotic and incompetent. Valve disease can be severely debilitating and even fatal if left untreated, particularly if the diseased valve is the mitral valve (between the left atrium and left ventricle) or the aortic valve (between the left ventricle and the aorta). According to recent estimates, more than 80,000 patients are diagnosed with aortic or mitral valve disease in U.S. hospitals each year.

Various surgical techniques may be used to repair a diseased or damaged valve. One repair technique which has been shown to be effective in treating incompetence, particularly of the mitral and tricuspid valves, is annuloplasty, in which the effective size of the valve annulus is contracted by attaching a prosthetic annuloplasty ring to an interior wall of the heart around the valve annulus. The annuloplasty ring comprises an inner substrate of a metal such as stainless or titanium, or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Annuloplasty rings may also be utilized in combination with other repair techniques such as quadrangular resection, in which a portion of a valve leaflet is excised, the remaining portions of the leaflet are sewn back together, and a prosthetic annuloplasty ring is then attached to the valve annulus to maintain the contracted size of the valve. Other valve repair techniques in current use include commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of the valve leaflets or annulus. Annuloplasty rings may be used in conjunction with any repair procedures where contracting or stabilizing the valve annulus might be desirable.

In cases where a cardiac valve is not suited to repair, the valve may be replaced, by excising the valve leaflets of the natural valve, and securing a replacement valve in the valve position, usually by suturing the replacement valve to the natural valve annulus. Various types of replacement valves are in current use, including mechanical and biological prostheses, homografts, and allografts, as described in Bodnar and Frater, Replacement Cardiac Valves 1-357 (1991). A comprehensive discussion of heart valve diseases and the surgical treatment thereof is found in Kirklin and Barratt-Boyes, Cardiac Surgery 323-459 (1986).

Using current techniques, most valve repair and replacement procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, so as to arrest cardiac function. In some cases, cardioplegic fluid is injected into the coronary sinus for retrograde perfusion of the myocardium. The patient is placed on extracorporeal cardiopulmonary bypass to maintain peripheral circulation of oxygenated blood.

Of particular interest in the present application are techniques for the repair and replacement of the mitral valve. The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position accessible through the sternotomy. An opening, or atriotomy, is then made in the right side of the left atrium, anterior to the right pulmonary veins. The atriotomy is retracted by means of sutures or a retraction device, exposing the mitral valve directly posterior to the atriotomy. One of the forementioned techniques may then be used to repair or replace the valve.

An alternative technique for mitral valve access may be used when a median sternotomy and/or rotational manipulation of the heart are inappropriate. In this technique, a thoracotomy is made in the right lateral side of the chest, usually in the region of the fourth or fifth intercostal space.

One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

What is needed, therefore, are devices and methods for carrying out heart valve repair and replacement as well as other procedures within the heart and great vessels that reduce the trauma, risks, recovery time and pain that accompany current techniques. The devices and methods should facilitate surgical intervention within the heart or great vessels without the need for a gross thoracotomy, preferably through small incisions within intercostal spaces of the rib cage, without cutting, removing, or significantly deflecting the patient's ribs or sternum. In particular, the devices and methods should allow for removal of tissue from the thoracic cavity, as well as for introduction of surgical instruments, visualization devices, annuloplasty rings, replacement valves, and the like into the thoracic cavity, to facilitate heart valve repair and replacement. The devices and methods should enable the implantation of annuloplasty rings of various shape, size, and stiffness. In addition, the devices and methods should facilitate replacement of a heart valve with various types of prostheses, including mechanical and biological prostheses, homografts, and allografts.

SUMMARY OF THE INVENTION

The invention provides devices and methods for performing less-invasive surgical procedures within an organ or vessel, and particularly, within the heart and great vessels of the thoracic cavity. The devices and methods of the invention facilitate intervention within the heart and great vessels without the need for a median sternotomy or other form of gross thoracotomy, substantially reducing trauma, risk of complication, recovery time, and pain for the patient. Using the devices and methods of the invention, surgical procedures may be performed through percutaneous penetrations within intercostal spaces of the patient's rib cage, without cutting, removing, or significantly displacing any of the patient's ribs or sternum. The devices and methods are particularly well-adapted for heart valve repair and replacement, facilitating visualization within the patient's thoracic cavity, repair or removal of the patient's natural valve, and, if necessary, attachment of an annuloplasty ring or a replacement valve in the natural valve position. The invention facilitates valve repair with a variety of different annuloplasty rings, as well as valve replacement with any of a variety of replacement valves, including mechanical prostheses, bioprostheses, homografts, and allografts.

According to the invention, access into the chest cavity and into the heart is obtained by means of small incisions, punctures, cannulae, trocars, or other percutaneous penetrations of minimal size positioned in the intercostal spaces between adjacent ribs of the rib cage. In this application, these percutaneous penetrations within intercostal spaces will be referred to as "intercostal ports". The intercostal ports utilized in the present invention will not require removal, cutting, or other modification of the ribs or sternum, and will generally avoid any significant retraction of the ribs, other than the incidental deflection of the ribs which may occur when a cannula, trocar, or other means of tissue retraction is placed in an intercostal space. Such retraction of ribs will generally be avoided entirely, and if occurring at all, will be limited to deflection of less than about one centimeter. Preferably, all such intercostal ports will have a width (or diameter, if round) of less than 30 mm in order to fit within an intercostal space without significant rib retraction, and in many cases will have a width of less than 12 mm so as to minimize trauma.

In a first aspect, the invention provides a method of closed-chest repair of a heart valve. Utilizing the method of the invention, the patient's heart is arrested and cardiopulmonary bypass is established. The interior of the patient's chest cavity is viewed by means of a thoracoscope or by directly looking through a cannula or other retracting means positioned in an intercostal space. A knife or scissors is introduced through an intercostal port into the patient's chest, and the cutting means is used to first form an opening in the pericardium, then to form a cardiac penetration in a wall of the heart. One or more percutaneous cannulae, trocars, or other means of retracting tissue may be positioned in an incision or puncture within an intercostal space through which various instruments may be introduced into the chest cavity. These instruments may be positioned through the cardiac penetration to perform, for example, annuloplasty, quadrangular resection of valve leaflets, commissurotomy, reattachment of chordae tendonae or papillary muscle tissue, shortening of chordae tendonae, decalcification, and the like. Advantageously, all of these steps may be performed without cutting, removing, or substantially retracting the ribs or sternum, eliminating the pain, trauma, long recovery time, and complications associated with gross thoracotomy.

The patient's heart is preferably arrested by occluding the patient's aorta between the patient's coronary ostia and the patient's brachiocephalic artery with an expandable member on a distal end of an endovascular aortic catheter introduced through a peripheral artery such as a femoral artery. Cardioplegic fluid is then delivered through a lumen in the catheter into the patient's aorta upstream of the expandable member to arrest cardiac function. Alternatively, or in addition to such antegrade cardioplegic fluid delivery, cardioplegic fluid may be delivered in a retrograde manner by means of a catheter positioned in the coronary sinus of the patient's heart. In an alternative approach, an external cross-clamp may be placed thoracoscopically on the aorta through a small incision or cannula in the patient's chest. Cardioplegic fluid may be delivered either through a cannula introduced thoracoscopically and inserted through the aortic wall, or through an endovascular aortic catheter extending from a peripheral artery into the ascending aorta upstream of the cross-clamp.

In a preferred embodiment of the method, a prosthetic annuloplasty ring is introduced through an intercostal port and into an internal chamber of the heart, and the ring is attached to the heart wall around the annulus of the valve within the internal chamber. Usually, the valve will first be sized by introducing a sizing device through the intercostal port and into the heart through the cardiac penetration, and positioning the sizing device adjacent to the valve to measure its size. A valve sizing disk attached to an elongated shaft or handle may be used for this purpose. Once the valve size has been determined, sutures are inserted in the native valve annulus and an annuloplasty ring of appropriate size is selected. The ring is attached to an elongated handle and the ring is introduced through an intercostal port and through the cardiac penetration into the heart. The annuloplasty ring is then secured to the annulus of the heart valve, by tying knots in the sutures extracorporeally and pushing the knots into the heart with an elongated knot-pusher. The sutures are preferably applied to the annuloplasty ring outside of the chest cavity, and the ring is slid along the sutures through the intercostal port and cardiac penetration up to the valve annulus. The sutures are then tied and rimmed using thoracoscopic instruments.

One advantage of the method of the invention is that it allows the surgeon to obtain access to the valve through an intercostal port and a cardiac penetration, assess the nature and extent of valve disease, and then decide whether to repair or replace the valve. If the disease is such that repair is inappropriate, the surgeon may elect to replace the valve with any of a variety of replacement valves. A valve replacement method according to the invention may include the step of removing all or part of the patient's natural heart valve by means of a cutting tool introduced through an intercostal port and through the cardiac penetration into the heart. The method further comprises the step of introducing a replacement valve through an intercostal port and through the cardiac penetration into the internal chamber of the heart. The replacement valve is then fastened within the heart, usually by means of a suturing instrument introduced through an intercostal port and through the cardiac penetration. As with the annuloplasty method described above, sutures are usually applied to the valve outside of the chest, and the valve is slid along the sutures into the heart. The sutures are then tied and trimmed. The method may further include the step of sizing the patient's heart valve before the replacement valve is introduced. In an exemplary embodiment, a sizing instrument is introduced through an intercostal port and through the cardiac penetration to measure the size of the valve annulus and to determine the size of the replacement valve.

In order to suture the annuloplasty ring or replacement valve to the interior of the heart, the sutures are preferably applied to the heart tissue, drawn out of the patient's body through an intercostal port and then applied to the annuloplasty ring or replacement valve. The sutures may be radially arranged in spaced-apart locations about an organizer ring disposed outside of the patient's body. The sutures are then held in tension as the annuloplasty ring or replacement valve is introduced into the interior of the heart and positioned in the natural valve position. The annuloplasty ring or replacement valve may be introduced by means of a specialized holder attached to an elongated handle, or simply pushed along the sutures into the chest cavity by means of the surgeon's hands, then into the native valve position using conventional thoracoscopic instruments such as forceps or needle drivers.

In a particularly preferred embodiment, the heart valve comprises a mitral valve which is disposed between the left atrium and left ventricle of the patient's heart. An intercostal port is created within an intercostal space in a right lateral portion of the patient's chest, usually within the third, fourth, or fifth intercostal space. From this intercostal port, a cardiac penetration may be formed in the wall of the left atrium at a location which is generally aligned with the intercostal port. In this way, surgical instruments may be introduced from the intercostal port in the right chest to form the cardiac penetration, repair or excise the patient's natural valve, and/or introduce and attach an annuloplasty ring or replacement valve.

In a further aspect of the invention, a system is provided for repairing a heart valve. The system includes an annuloplasty device and a device holder for releasably holding the annuloplasty device to facilitate introducing it through an intercostal port and into the heart. The device holder includes connection means for connecting the holder to an elongated handle. The connection means is configured to connect to the handle such that the handle, holder, and annuloplasty device together have a profile with a profile height smaller than the width of the intercostal space, usually less than about 30 mm and preferably less than about 25 mm. The annuloplasty device has a bottom side which is positioned in contact with the wall of the heart around the heart valve when the device is implanted. The bottom side defines a first plane which is generally perpendicular to a longitudinal (axial) axis of the annuloplasty device. In an exemplary configuration, the connection means connects to the handle such that the longitudinal axis of the handle forms an angle with the first plane selected so that handle may be used to introduce the annuloplasty ring through the intercostal port without contacting or retracting the ribs adjacent the intercostal port. The angle will usually be about 0°+/−45°, and preferably 0°+/−20°, but could also be outside of this range if the annuloplasty device is small relative to the size of the intercostal space.

The holder also includes a means for retaining the annuloplasty device on the holder, such as retention sutures, a retaining clip, or a pivoting leaf on the holder. The system may further include means for releasing the annuloplasty device from the holder, such as a cutting device for cutting the retention sutures which hold the annuloplasty device on the holder, or other device for releasing the mechanism which secures the annuloplasty device to the holder.

The annuloplasty device may be any of the commercially-available annuloplasty rings, may be either stiff or flexible, split or continuous, and may have any of a variety of shapes, including C-shaped, D-shaped, kidney-shaped, saddle-shaped racetrack-shaped, oval, semi-circular, and circular. The annuloplasty device may also be malleable or shapable into a desired shape, or may be flexible and resilient and secured in the heart in a shape which differs from its natural, unstressed shape.

The valve repair system may further include an elongated handle having a distal end mounted to the device holder and a proximal end opposite the distal end. The handle is configured to introduce the annuloplasty device into the patient's heart through an intercostal port. Preferably, the handle is at least about 20 cm in length to allow positioning the annuloplasty device in the left atrium of the heart from a right lateral portion of the patient's chest.

The handle may also include means for pivoting the annuloplasty device from a first orientation for introduction through the intercostal space to a second orientation for attachment in the patient's heart. The pivoting means is configured for actuation from a proximal end of the handle. In this way, the annuloplasty device may be introduced edge-first through the intercostal space, then pivoted about an axis generally perpendicular to the handle into an orientation suitable for attachment within the patient's heart, preferably wherein the first plane is perpendicular to the longitudinal axis of the handle.

While a variety of mechanisms may be utilized for connecting the holder to the handle, in an exemplary embodiment, the handle has a tongue pivotably coupled to its distal end, a movable actuator coupled to its proximal end, and a rod or cable extending through a lumen in the handle connecting the actuator to the tongue. The tongue is received in an aperture in the device holder, and includes a spring catch or other means for retaining the tongue in the aperture. The aperture has an open proximal end, a distal end opposite the proximal end, and an axis therebetween defining the direction in which the tongue is received in the aperture. The aperture is preferably oriented so that the axis forms an angle of 0°+/−45° relative to the first plane of the annuloplasty device, facilitating introduction through an intercostal port. In this way, the tongue may be aligned with the longitudinal axis of the handle for edge-first introduction of the annuloplasty device through the intercostal port, then pivoted to an appropriate angle, usually about 90°, relative to the handle so that the first plane of the annuloplasty device is generally parallel to the interior wall of the heart to which it is to be attached.

As an alternative to pivoting the annuloplasty device, the annuloplasty device and device holder may be flexible, collapsible, or compressible so that it may be deformed or constrained into a shape which allows the device and holder to be introduced through an intercostal space into the thoracic cavity.

The system of the invention may also include a retraction means for retracting the chest wall tissue in a percutaneous penetration within an intercostal space, to facilitate introduction of instruments, visualization devices, valve sizers, annuloplasty devices, and replacement valves through the penetration without interference and without damaging tissue. The retraction means displaces the tissue around the percutaneous penetration to create a small opening, but does not significantly retract or deflect the ribs. The retraction means may comprise any of various types of tissue or wound retractors, but in a preferred embodiment comprises a cannula having a distal end positionable through the intercostal space and an inner lumen of sufficient size and shape to allow a replacement valve or annuloplasty device to be positioned through the cannula into the chest cavity. Preferably, the inner lumen has a width of between about 12 mm and about 30 mm, in order to allow the cannula to be positioned within the intercostal space with the ribs unretracted, while allowing the annuloplasty device or replacement valve to pass through the lumen with sufficient clearance. The inner lumen has a height of at least 25 mm, and usually at least 35 mm, to permit introduction of the annuloplasty device or replacement valve. Usually, the height is larger than the width, in a preferred embodiment, at least about 1.5 times the width. In this way, the annuloplasty device or replacement valve may be introduced in an edge-first manner through the lumen of the cannula, then pivoted 90° into a face-first orientation for attachment within the heart.

Because the annuloplasty device or replacement valve may be attached within the heart with a plurality of individual sutures, the system may further include means for organizing sutures outside of the chest cavity. The suture organizing means preferably is attached to the proximal end of the access cannula described above, and comprises a plurality of slots arranged radially about the inner lumen of the cannula. In this way, as each suture is placed in the heart tissue, the free ends of the suture may be withdrawn through the lumen of the access cannula and placed in one of the slots. The free ends may then be placed through the sewing ring of the annuloplasty device or replacement valve, and the device or valve advanced through the inner lumen of the cannula and into the heart by sliding along the suture threads.

Preferably, the annuloplasty device is premounted to the device holder and the two are sterilized and packaged together in a sterile pack. In this way, the pack may be opened in the sterile operating room environment with the annuloplasty device and holder ready for immediate use. In some embodiments, the elongated delivery handle, sizing disks, access cannula or other retraction means, suture organizer, and/or other system components may be included in the sterile pack with the annuloplasty device and holder. Alternatively, the annuloplasty device could be packaged separately from the device holder and the device mounted to the holder in the operating room at the time of the valve repair procedure.

The delivery handle of the invention is configured not only for introducing the annuloplasty device through an intercostal port into the heart, but for introducing valve sizing devices and/or a replacement valve as well. In this way, the same handle may be used to first size the native valve, then to introduce an annuloplasty device to repair the mitral valve, or to introduce a replacement valve to replace the native valve.

Accordingly, the invention also provides a device for sizing a valve which includes both an elongated handle and a sizing disk attached to the distal end of the handle. The sizing disk is configured to connect to the handle in an orientation in which the handle and the sizing disk together have a profile with a profile height smaller than the width of the intercostal space through which the sizing disk is introduced, usually less than about 30 mm and preferably less than about 25 mm. In a preferred embodiment, the sizing disk is pivotably attached to the handle so that it may be introduced through the intercostal space in an edge-first orientation, and then pivoted into a face-first orientation for sizing the valve. The handle may have, as described above, a tongue pivotably mounted to its distal end which is received in an aperture on the sizing disk, allowing the sizing disk to be oriented with its face generally parallel to the longitudinal axis of the handle for introduction, then perpendicular to the longitudinal axis for sizing the valve. For sizing a valve for an annuloplasty repair, the sizing disk usually has a shape corresponding generally to the natural shape of the native valve annulus, which is roughly oval, kidney-shaped or D-shaped. The sizing disk also includes notches or markings to measure the spacing between the trigones or commisures of the valve. For valve replacement procedures, the sizing disk is preferably round, corresponding to the shape of the replacement valve sewing ring.

The invention further provides a holder for a prosthesis for repairing or replacing a heart valve. The holder may be adapted for holding either an annuloplasty ring or a prosthetic heart valve. The holder includes a holder body having a top, a bottom, and a holder axis. A holding means is included on the holder body for releasably holding a prosthesis such that the central axis of the attachment ring of the prosthesis is approximately parallel to the holder axis. The holder further includes a connection means for connecting to an elongated handle for introducing the holder and prosthesis through an intercostal space. The connection means has a proximal end, a distal end, and a connection axis therebetween. The connection means is positioned on the holder body such that the connection axis is oriented at an angle relative to the holder axis selected so that, when the prosthesis is held by the holding means, the profile of the prosthesis and holder perpendicular to the connection axis has a height less than the width of the intercostal space, usually less than about 30 mm and preferably less than about 25 mm.

In a preferred embodiment, as described above, the handle has a pivotable tongue on its distal end, and the connection means comprises an aperture for receiving the tongue. The aperture has an open proximal end through which the tongue is received in a direction parallel to the connection axis. Alternatively, the connection means may comprise a threaded hole, snap fitting, luer fitting, threaded shaft, or tongue configured to connect to a complementary connector on the handle. Preferably, the connection means is removable from the handle to allow valve sizers, annuloplasty rings, and replacement valves to be interchanged on the same handle. However, the handle and holder may alternatively be permanently inseparably interconnected for dedicated use with a single annuloplasty device or replacement valve.

A further understanding of the nature and advantages of the invention may be realized by reference to the remaining portions of the specification and the drawings.

BRIEF DESCRIPTION OF THE DRAWINGS

FIGS. 5A–5C are perspective, front and side views respectively of an annuloplasty ring holder constructed in accordance with the principles of the invention.

FIGS. 6A, 7A, and 8A are top elevational views of various embodiments of an annuloplasty device constructed in accordance with the principles of the present invention.

FIGS. 6B, 7B, and 8B are perspective views of various holders for the annuloplasty devices of FIGS. 6A, 7A, and 8A, respectively.

FIGS. 6C, 7C and 8C are perspective views of the holders of FIGS. 6B, 7B, and 8B holding the annuloplasty devices of FIGS. 6A, 7A, and 8A, and attached to a distal portion of the delivery handle of FIG. 1.

FIGS. 9A, 9B and 9C are side cross-sectional views of various alternative embodiments of annuloplasty device holders constructed according to the principles of the invention, schematically illustrating the introduction of the holder through an intercostal space between two ribs.

FIGS. 10A–10D are bottom, side transverse cross-sectional, front transverse cross-sectional, and top views, respectively, of an annuloplasty ring and holder according to the invention in an alternative embodiment thereof, a pair of ring retention leafs of the holder being in a closed position.

FIGS. 10E–10F are bottom and front transverse cross-sectional views, respectively, of the annuloplasty ring and holder of FIGS. 10A–10D with the ring retention leafs in an open position.

FIG. 10G is a perspective view of a leaf actuation instrument for moving the ring retention leafs of the holder of FIGS. 10A–10F.

FIGS. 12A–12B are perspective views of two embodiments of an annuloplasty ring holder assembly according to the invention.

FIGS. 13A–13C are front, top and side views, respectively, of an adaptor for an annuloplasty ring holder in accordance with the invention.

FIGS. 14A–14C are front, top and side views, respectively, of an additional embodiment of an adaptor for an annuloplasty ring holder in accordance with the invention.

FIG. 26A–26C are perspective, top and front views, respectively, of a holder for a prosthetic valve constructed in accordance with the principles of the invention.

FIG. 27 is a front view of the prosthetic valve of FIGS. 26A–26C illustrating the pivoting of distal and proximal pieces thereof.

FIG. 28 is a perspective view of a prosthetic valve which may be held by the holder of FIGS. 26A–26C.

FIG. 29 is a perspective view of the prosthetic valve of FIG. 28 held on the holder of FIG. 27.

DETAILED DESCRIPTION OF THE PREFERRED EMBODIMENTS

The present invention provides various devices and systems for less-invasive surgical treatment of cardiac valves, and methods of using the devices and systems. The systems may be adapted either for cardiac valve repair, wherein a prosthetic annuloplasty ring is attached to an internal wall of the heart around the native valve annulus, or for cardiac valve replacement, wherein the native valve is replaced with a replacement valve, usually a prosthetic valve. The system includes, as described in detail below, a delivery handle for positioning the repair or replacement prosthesis through an intercostal space and into the interior of the heart, and a prosthesis holder, preferably attached to the end of the delivery handle, for releasably holding the repair or replacement prosthesis. In various embodiments, the system may include the repair or replacement prosthesis itself, devices for sizing the native valve, devices for retracting tissue within an intercostal space to facilitate introduction of the prosthesis, devices for organizing the sutures used to attach the prosthesis within the heart, and other components. Each of these components will now be described, followed by a description of a preferred method of using the system in a patient.

The system and method of the invention facilitate repairing or replacing a cardiac valve without requiring a median sternotomy or other gross thoracotomy, and without the substantial retraction of the ribs common in conventional open-chest valve treatment procedures. To accomplish this, the system is configured to operate through "intercostal ports," which, as discussed above, is used herein to include small incisions, punctures, or other types of percutaneous penetrations positioned in the intercostal spaces of the rib cage with the ribs in their natural, substantially unretracted positions. Cannulae, trocars, or other types of tissue retraction devices may be positioned in the percutaneous penetrations to facilitate introduction of instruments, visualization devices, prostheses, and the like, but these will generally be limited in size to the width of the intercostal space (e.g. less than about 30 mm), and will not require retraction of the ribs. In some cases, a slightly oversized cannula or retractor may be used, but even in these cases retraction of the ribs will be limited to less than about one centimeter. In this way, the pain, trauma, and complications associated with rib removal and/or gross rib retraction may be eliminated.

Figure 1:
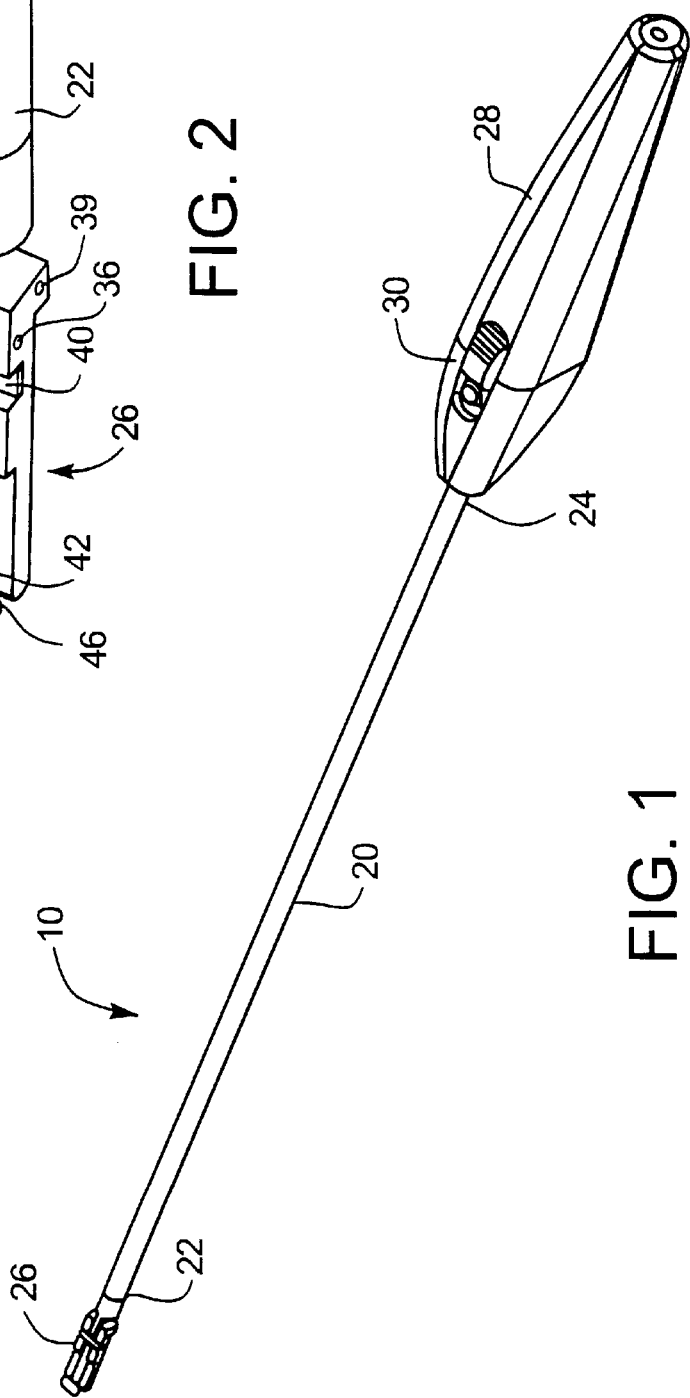
FIG. 1 is a perspective view of a delivery handle for a cardiac valve sizer, annuloplasty ring, or valve prosthesis constructed in accordance with the principles of the present invention.

FIGS. 1–4 illustrate a delivery handle for delivering a prosthesis mounted on a holder through an intercostal space and into the interior of the heart. As shown in FIG. 1, delivery handle 10 comprises a shaft 20 having a distal end 22 and a proximal end 24. A holder coupling 26 is mounted to distal end 22, and a handle 28 is mounted to proximal end 24. A slidable actuation button 30 is mounted to handle 28 and is linked to holder coupling 26 as described below, so that moving actuation button 30 pivots holder coupling 26.

Figure 2:
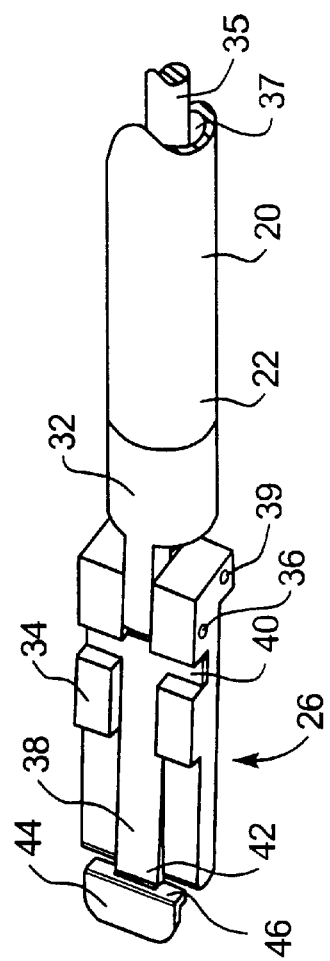
FIG. 2 is a perspective view of a distal portion of the delivery handle of FIG. 1.

As shown in FIG. 2, in a preferred embodiment, holder coupling 26 comprises a base 32 mounted to distal end 22 of shaft 20. A bifurcated tongue 34 is pivotably mounted to base 32 by a transverse pin 36. A rod 35 extends through a lumen 37 in shaft 20 and is pinned to tongue 34 by a second transverse pin 39. A leaf spring 38 has a proximal crosspiece 40 attached to tongue 34, and a free distal end 42 to which is attached a catch 44 stepped outwardly and upwardly from leaf spring 38 to define a proximally-facing surface 46. Catch 44 serves to retain a prosthesis holder on holder coupling 26, as described below.

Shaft 20 and holder coupling 26 are configured for positioning through an intercostal port into the chest cavity (without retracting the ribs), and preferably have a cross-sectional of width less than about 30 mm. In an exemplary embodiment, shaft 20 is about 4–8 mm in diameter, and tongue 34 has a transverse width of about 4–6 mm and a transverse height of about 0.5–2.0 mm. Shaft 20 has a length selected so that holder coupling 26 may be positioned within the heart near the native valve to be repaired or replaced, with shaft 22 extending through the desired intercostal port and handle 28 disposed outside of the patient's chest. In a preferred embodiment, shaft 20 is configured to reach the mitral valve, disposed between the left atrium and left ventricle of the heart, from an intercostal port in the right lateral side of the patient's chest between the second and sixth intercostal spaces. For most cases, shaft 20 has a length of at least about 20 cm, and preferably at least about 30 cm, but may vary according to patient size and according to the valve to be repaired and the approach taken to access the valve. Shaft 20, handle 28, and holder coupling 26 are preferably made of stainless steel, titanium, aluminum, or a stiff biocompatible polymer.

Figure 3:
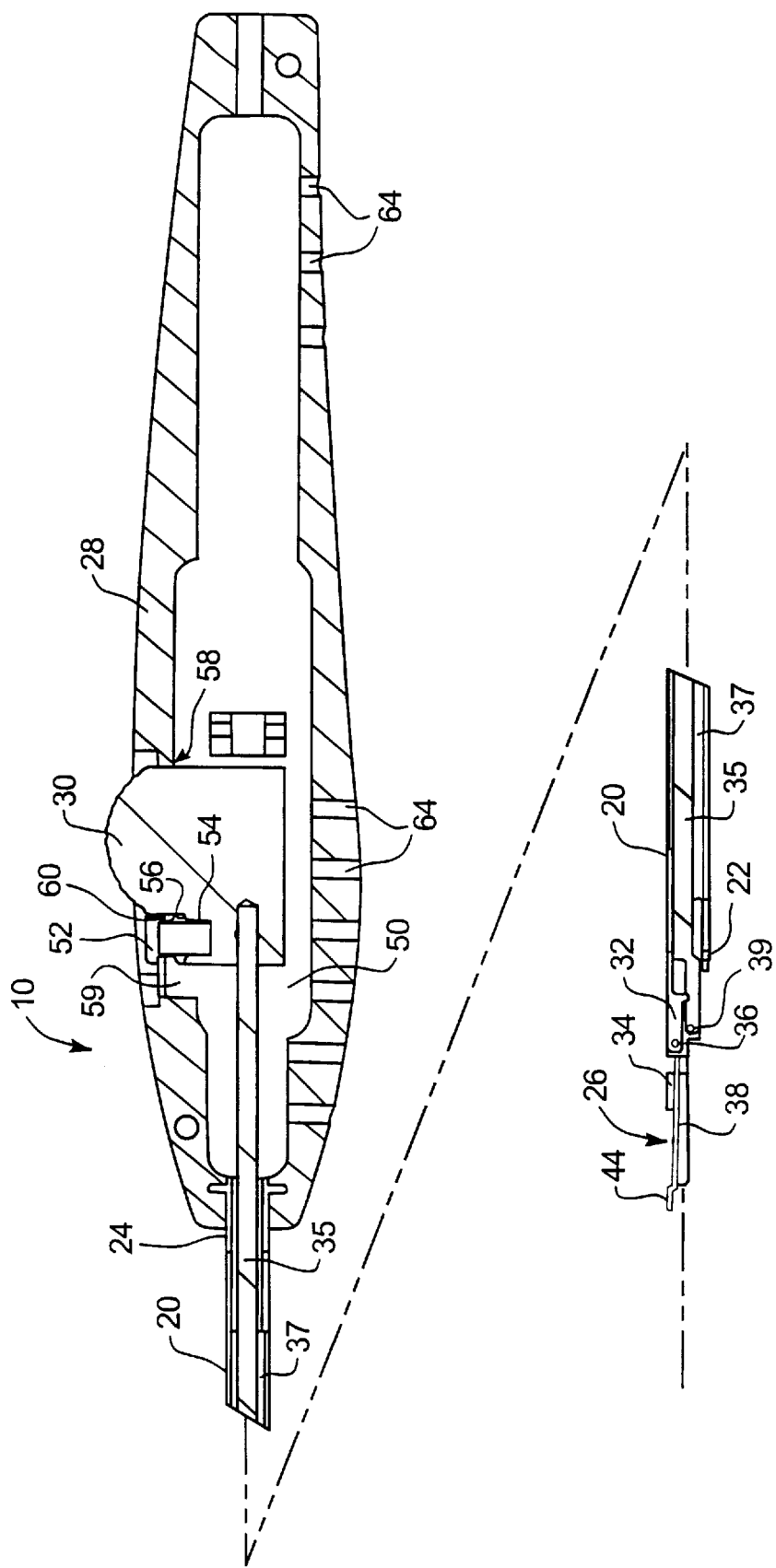
FIG. 3 is a side cross-sectional view of the delivery handle of FIG. 1 with a holder coupling at the distal end of the delivery handle in a longitudinally-aligned orientation.
Figure 4:
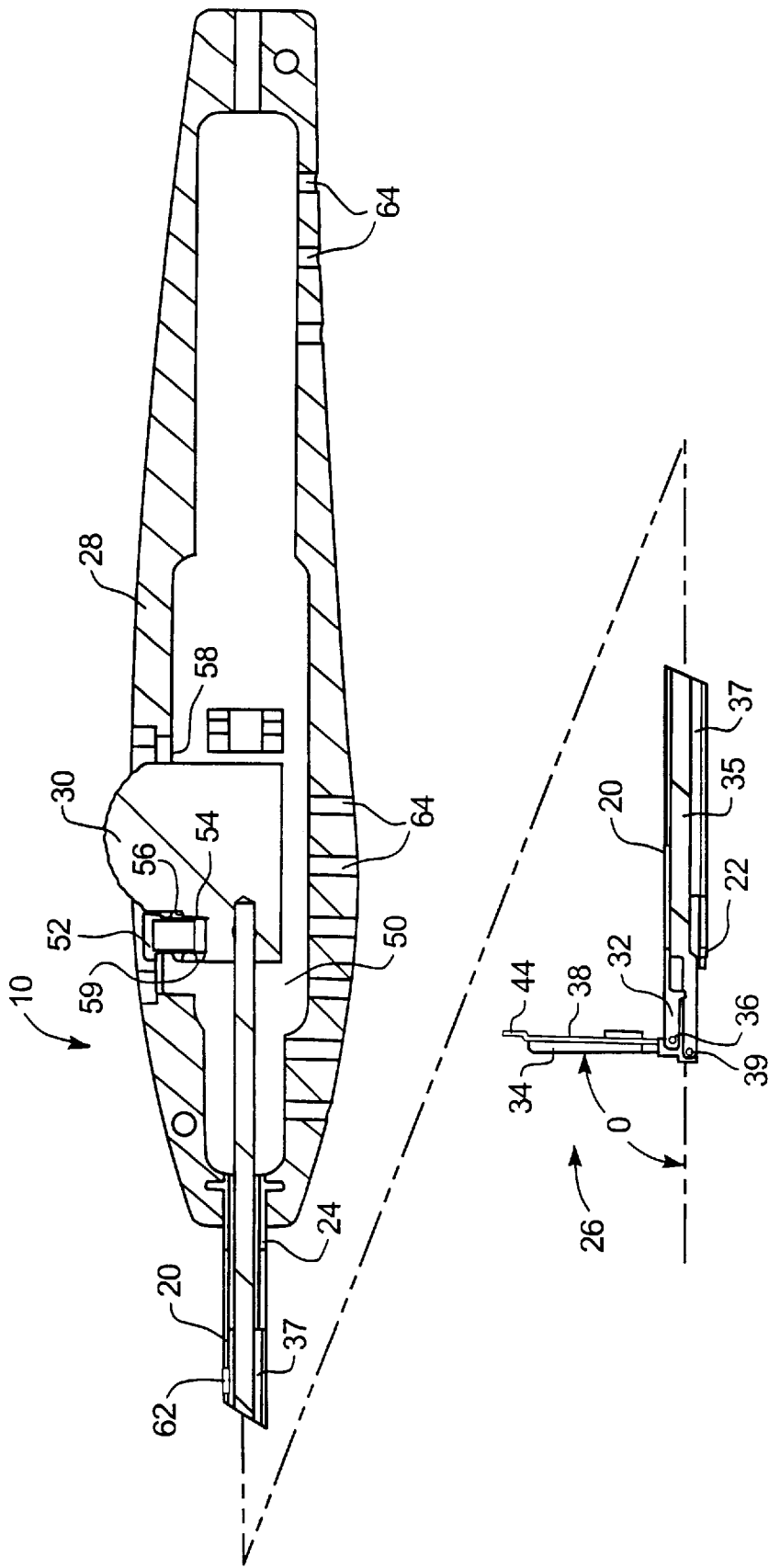
FIG. 4 is a side cross-sectional view of the delivery handle of FIG. 1 with a holder coupling at the distal end of the delivery handle pivoted into a transverse orientation.

Referring now to FIGS. 3–4, rod 35 extends proximally from holder coupling 26 through lumen 37 of shaft 20 into the interior 50 of handle 28, where it is attached to a lower portion of actuator button 30. Rod 35 is thus axially movable in tandem with actuator button 30. A lock button 52 is slidably mounted within a bore 54 in actuator button 30 and is biased upward by a coil spring (not illustrated). Lock button 52 includes an annular flange 56 having a tapered upper edge which engages an inner surface 58 of handle 28, holding lock button 52 in a downward position when actuator button 30 is in the proximal position of FIG. 3. When actuator button 30 is slid distally to the position of FIG. 4, flange 56 is aligned with an aperture 59, allowing lock button 52 to be urged upward. In this position, actuator button 30 is prevented from moving proximally due to the engagement of flange 56 with a proximal surface 60 of aperture 59 (best seen in FIG. 3). When it is desired to return actuator button 30 to the proximal position, lock button 52 is pushed downward until flange 56 clears proximal surface 60, allowing actuator button 30 to slide proximally. It should be noted that various types of actuators may be used for translating rod 35, such as levers, rotatable knobs, and push buttons. Moreover, the provision of lock button 52 is optional, and in some cases it may be more desirable to eliminate lock button 52 so that actuator button 30 is free to move distally and proximally without locking. Lock button 52 could also be configured to lock actuator button 30 in both the proximal and distal positions, or in various intermediate positions.

When actuator button 30 is in the proximal position of FIG. 3, holder coupling 26 is preferably longitudinally aligned with the longitudinal axis of shaft 20. In this position, holder coupling 26 and shaft 20 have a transverse profile small enough that a prosthetic annuloplasty ring or valve on a holder, when mounted to holder coupling 26 as described below, may be positioned through an intercostal port into the chest cavity. Depending upon patient anatomy, patient size, prosthesis holder configuration, and prosthesis size, holder coupling 26 could be oriented at a range of angles between about 0° and 45° relative to the longitudinal axis of shaft 20 and still allow the prosthesis and holder to introduced through an intercostal port without significant retraction of the ribs.

When rod 35 is translated distally by moving actuator button 30, holder coupling 26 pivots about pin 36 through an angle θ relative to the longitudinal axis of shaft 20, as shown in FIG. 4. In order to orient a prosthetic annuloplasty ring or valve optimally for attachment within the heart, angle θ is preferably about 90°, however, angle θ may be any angle between about 45° and 135°, depending upon the particular valve being repaired or replaced, the location and size of the intercostal port through which delivery handle 10 is introduced, and the anatomy of the patient.

A cleaning port 62 is disposed in shaft 20 in communication with inner lumen 37 to facilitate delivery of a cleaning fluid into the interior 50 of shaft 20 and handle 28. A plurality of drain holes 64 are provided in the lower side of handle 28 to allow cleaning fluid to drain from the handle.

Holder coupling 26 is adapted for attachment to a valve sizing device or to a holder for a prosthetic annuloplasty ring or replacement valve. An exemplary embodiment of a holder for a prosthetic annuloplasty ring according to the invention is illustrated in FIGS. 5A–5C. Holder 70 includes a holder body 72 having an outer edge 74 with a shape selected to match that which the annuloplasty ring is to assume when secured within the heart, such as D-shaped, C-shaped, kidney-shaped, semicircular, oval, or circular. A groove or channel 76 having an upper flange 73 extends around outer edge 74 on the lateral side of holder body 72 and has a size and shape selected to receive the annuloplasty ring in order to hold the annuloplasty ring on holder body 72. One or more suture holes 77 extend through holder body 72 through which a suture may be threaded and tied around the annuloplasty ring to secure it to the holder. A groove or ridge 75 extends across top surface 78 transverse to the direction in which the retention sutures would be tied to holder 70. In this way, a knife may be guided by groove or ridge 75 to cut the sutures to release the ring from holder 70. Holder body 72 has a top surface 78 on which is disposed a handle coupling 80. In an exemplary embodiment, handle coupling 80 comprises a slot 82 configured to receive holder coupling 26 on delivery handle 10. Slot 82 has an open proximal end 84 and an open distal end 86. Holder coupling 26 is received into slot 82 through proximal end 84 and slides into slot 82 until catch 44 extends outside of slot 82 through distal end 86, as described more fully below.

Various exemplary annuloplasty rings which may be utilized in conjunction with holder 70 are illustrated in FIGS. 6A, 7A, and 8A. The annuloplasty rings preferably comprise a flexible, stiff, or deformable support ring covered by a fabric or mesh suitable for suturing the annuloplasty ring to heart tissue. The support ring may be a biocompatible metal such as stainless steel or titanium or a flexible material such as silicone rubber or Dacron cordage, depending upon the structural and performance characteristics desired in the ring. The overlying fabric or mesh may be a polyester knit fabric, polyester velour cloth, expanded polytetrafluoroethylene, or other biocompatible porous material with sufficient structural integrity to resist tearing when a suture is passed through it and secured to the heart. Holder 70 may be adapted for use with any of the various commercially available annuloplasty rings, including the Carpentier-Edwards™ Mitral Ring, the Carpentier PhySio™ Ring, or Cosgrove™ Ring available from Baxter Healthcare Corp., Edwards CVS Div., Irvine, Calif., the Sculptor™ or Duran™ Ring available from Medtronic, Inc. of Minneapolis, Minn., the Puig Massana™ Ring available from Sorin Biomedica of Salaggia, Italy, or the Biflex™ Ring available from St. Jude Medical, Inc. of St. Paul, Minn. Holder 70 is configured to hold annuloplasty rings of various shape and size. FIG. 6B illustrates a holder 70' adapted for holding the D-shaped split annuloplasty ring 90' shown in FIG. 6A, such as the Baxter, Inc. Carpentier-Edwards Mitral Ring. In FIG. 6C, annuloplasty ring 90' is mounted to holder 70', which is attached to holder coupling 26 of delivery handle 10. FIG. 7B illustrates a holder 70" adapted for holding the D-shaped continuous annuloplasty ring of FIG. 7A, such as the Baxter Carpentier PhySio™ Ring, or the Medtronic Sculptor™ Ring. FIG. 7C shows annuloplasty ring 90'" mounted to holder 70", which is attached to holder coupling 26 of delivery handle 10. FIG. 8B illustrates a holder 70'" adapted for holding the C-shaped split or open annuloplasty ring 90'" of FIG. 8A, which may be the Baxter Cosgrove™ Ring. FIG. 8C illustrates holder 70'" holding annuloplasty ring 90'" and mounted to holder coupling 26 of delivery handle 10. Annuloplasty rings of various other shapes may also be used with the holder of the invention, including kidney-shaped, saddle-shaped racetrack-shaped, semicircular, circular, and others. In some cases, the annuloplasty ring 90 may be flexible and may have a shape in a natural, unstressed condition which is different than the shape of holder 70. For example, a circular ring could be held by a D-shaped holder. In this way, the ring conforms to the shape of holder 70 and is held in the shape it will be in when secured within the heart. Ring 90 may also be shapable or malleable so that it may shaped into the shape of holder 70 and/or reshaped when secured within the heart.

As shown in FIG. 6A, annuloplasty ring 90' has a transverse height RH and a transverse width RW. In many cases, both transverse height RH and transverse width RW will be larger than the width of the intercostal space through which they are to be introduced. When mounted to holder 70, handle coupling 80 is adapted to receive holder coupling 26 such that an annuloplasty ring 90 can be attached to delivery handle 10 and introduced through an intercostal port without retraction of the adjacent ribs. In a preferred embodiment, slot 82 is parallel to a bottom side 88 of holder body 72, which is generally parallel to the plane contacting the bottom side of the annuloplasty ring when attached to holder 70. Such a configuration is illustrated in FIG. 9A, which schematically illustrates shaft 20 of delivery handle 10 positioning holder 70, to which is mounted an annuloplasty ring 90, within an intercostal space I between two ribs R (chest wall tissue is not shown for simplification). It may be seen that, when holder coupling 26 is longitudinally aligned with shaft 20, the bottom side 88 of holder 70, along with the plane containing the bottom side of annuloplasty ring 90, are parallel to the longitudinal axis of shaft 20 Alternatively stated, the longitudinal (or axial) axis of annuloplasty ring 90 is perpendicular to the longitudinal axis of shaft 20. In this configuration, holder 70, annuloplasty ring 90 and delivery handle 10 have a transverse profile of minimum size to facilitate introduction through intercostal space I. In most adult patients, intercostal space I will have a width W between about 20 mm and 30 mm in the right lateral chest at the locations suitable for approaching the mitral or tricuspid valve. Thus, with annuloplasty ring 90 mated to holder 70, the transverse height H between the bottom and top sides of holder 70, including the diameter shaft 20, will be less than about 30 mm, and preferably less than about 20 mm.

In addition to the configuration shown in FIG. 9A, handle coupling 80 of holder 70 may have various alternative configurations, two of which are shown in FIGS. 9B and 9C. In the embodiments of FIGS. 9B–9C, slot 82 is oriented at an angle α relative to bottom side 88 of holder body 72 (and the plane containing the bottom of annuloplasty ring 90 and perpendicular to the longitudinal axis of annuloplasty ring 90. Angle α is selected so that holder 70, with annuloplasty ring 90 mounted to it, may be attached to holder coupling 26 on shaft 20 and introduced through intercostal space I without retracting ribs R. Angle α may be either positive or negative relative to slot 82 (and the longitudinal axis of shaft 20), and is usually within a range of −45° to +45°, and preferably −20° to +20°. The height H of holder 70 perpendicular to bottom surface 88 will be substantially less than intercostal width W, usually less than about 25 mm, and preferably less than about 20 mm, so that some clearance is provided between holder 70 and the ribs R defining the intercostal space I. Once the holder and annuloplasty ring are through the intercostal space, delivery handle 10 may be manipulated and holder coupling 26 pivoted so that annuloplasty ring 90 is in an orientation suitable for advancement into and attachment within the heart, as described more fully below.

It should be noted that in some cases intercostal width W may be sufficiently large and the annuloplasty ring diameter (or width across the ring) sufficiently small that angle α could be as great as 90°—that is, bottom surface 88 (or the plane of ring 90) could form a right angle relative to the longitudinal axis of shaft 20—and ring 90 could still be positioned through the intercostal space without retracting the ribs significantly. However, in most cases it will be advantageous to orient the ring at an angle somewhat less than 90° relative to the longitudinal axis of shaft 20 to provide maximum clearance relative to the adjacent ribs and to allow the ring to be introduced through an intercostal port of minimum size.

FIGS. 10A–10G illustrate a further embodiment of an annuloplasty ring holder according to the invention. In this embodiment, holder 420 includes a holder body 422 having a top surface 424 and a bottom surface 426. A handle coupling 428 is mounted to top surface 424, and includes an axial slot 430 for receiving holder coupling 26 on delivery handle 10. A flange 432 extends around the top lateral edge of holder body 422. An annuloplasty ring 434, which may have various shapes, stiffnesses, and materials, is positionable around the lateral edge of holder body 422 abutting flange 432. A pair of ring retention leafs 436 are rotatably coupled to holder body 422 by a bearing 438 so as to be rotatable about an axis parallel to the longitudinal axis of annuloplasty ring 434. Each ring retention leaf 436 has a pair of apertures 440 in a top surface thereof for engagement by a leaf actuation instrument 442, shown in FIG. 10G. Leaf actuation instrument 442 has an elongated shaft 444 long enough to reach the native valve position in the heart from outside of the chest cavity (e.g. about 30 cm), and a pair of prongs 446 at its distal end for insertion into apertures 440 in ring retention leafs 436. A stop 448 extends downwardly from bottom surface 426 of holder body 422 to limit the rotation of ring retention leafs 436 beyond the open and closed positions. A lip 449 extends from bottom surface 426 to help retain ring 434 against flange 432. In this way, ring retention leafs 436 may be placed in the open position of FIGS. 10E–10F for placement of annuloplasty ring 434 on holder 420, and, using leaf actuation instrument 442, leafs 436 may be rotated into the closed position of FIGS. 10A–10C to trap ring 434 between leafs 436 and flange 432. After annuloplasty ring 434 has been secured around the native valve within the heart, leaf actuation instrument 442 may be introduced through an intercostal port and inserted into apertures 440 to rotate ring retention leafs 436 into the open position, releasing ring 434 from holder 420.

Figure 11A:
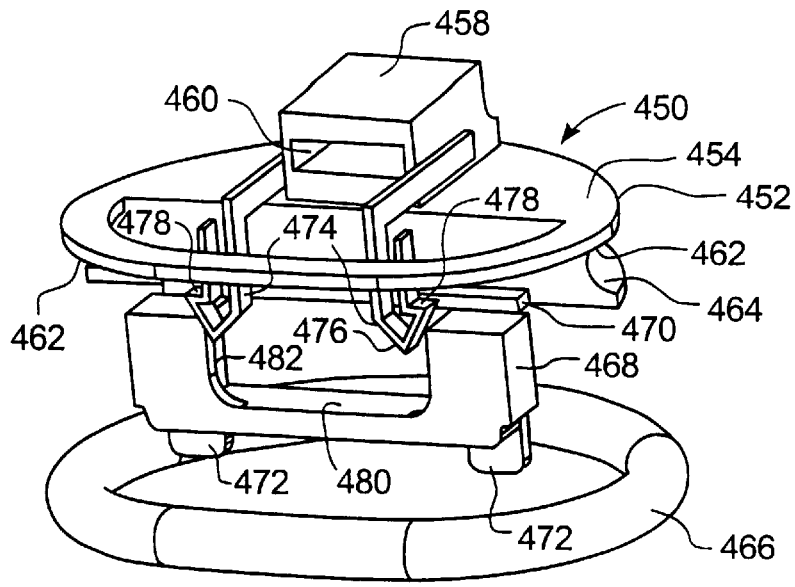
FIG. 11A is a perspective view of an annuloplasty ring and holder according to the invention in a further alternative embodiment thereof, with a ring retaining leaf of the holder in an open position.
Figure 11B:
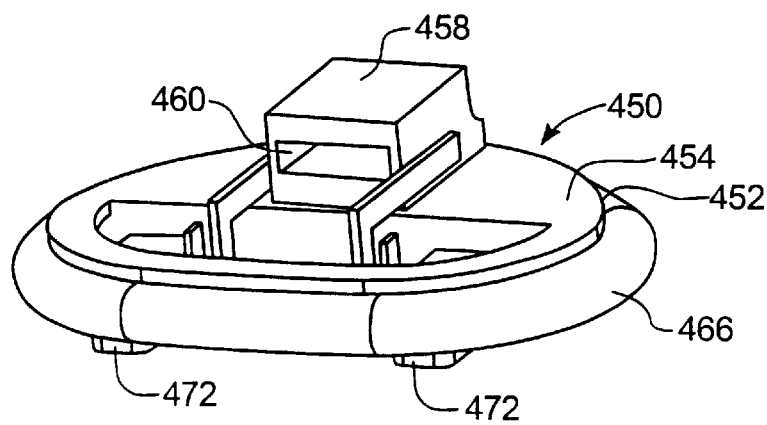
FIG. 11B is a perspective view of the annuloplasty ring and holder of FIG. 11A with the ring retention leaf in a closed position.
Figure 11C:
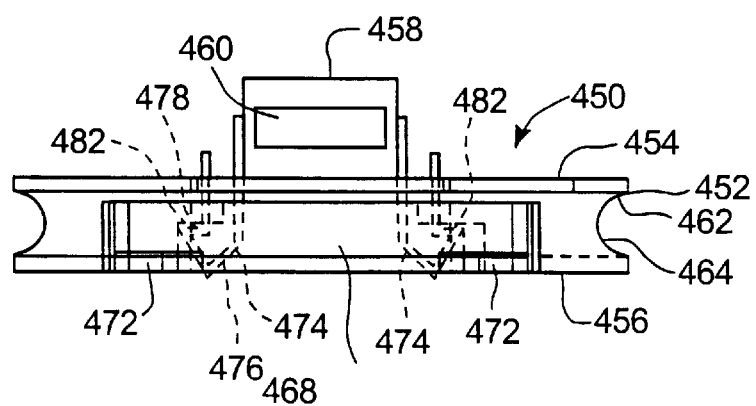
FIG. 11C is a front view of the holder of FIGS. 11A–11B with the ring retention leaf in a closed position.

An additional embodiment of an annuloplasty ring holder according to the invention is shown in FIGS. 11A–11C. Holder 450 comprises a holder body 452 having a top surface 454 and a bottom surface 456. A handle coupling 458 is mounted to top surface 454 and includes an axial slot 460 for receiving holder coupling 26 on delivery handle 10. A flange 462 extends around the top lateral edge of holder body 452, and a groove or channel 464 extends around the lateral side of holder body 452 on a rearward portion thereof. An annuloplasty device 466, which again could be of various shapes, stiffnesses, and materials, may be positioned around holder body 452 in channel 464, so as to abut flange 462. A ring retention leaf 468 is hingedly mounted to bottom surface 456 by a suitable coupling means, such as a living hinge 470 or by a pinned hinge joint, whereby ring retention leaf 468 may be pivoted between the open position of FIG. 11A to the closed position of FIGS. 11B–11C. A pair of tabs 472 extend from an outer edge of ring retention leaf 468 such that, when leaf 468 is in the closed position of FIG. 11B, ring 466 is trapped between tabs 472 and flange 462. Ring retention leaf 468 is retained in the closed position by a pair of flexible catches 474 which may be deflected toward each other by applying a laterally-directed force. Each catch 474 has a tapered distal end 476 leading proximally to a step 478. Ring retention leaf 468 has a central opening 480 through which catches 474 may extend when leaf 468 is in the closed position, and a shelf 482 for engaging steps 478 to retain leaf 468 in the closed position. Thus, when leaf 468 is pivoted from the open position to the closed position, the tapered distal ends of catches 474 engage leaf 468 at the edge of opening 480 and are urged inwardly as the leaf is closed. When leaf 468 is completely closed, steps 478 clear shelf 482 and catches 474 spring outwardly so that steps 478 engage shelf 478, maintaining leaf 468 in the closed position. After annuloplasty ring 466 has been secured around the native valve in the heart, thoracoscopic forceps or other elongated grasping device may be introduced through an intercostal port and used to squeeze catches 474 together, allowing leaf 468 to open and releasing annuloplasty ring 466 from holder 450.

Two additional embodiments of an annuloplasty ring holder assembly according to the invention are illustrated in FIGS. 12A–12B. In these embodiments, holder assemblies 100, 101 comprise a holder 102, 103 similar to the holders used with commercially-available annuloplasty rings, and an adaptor 104, 105 for attaching holder 102 to delivery handle 10. Holder 102,103 is in some respects similar to holder 70 of FIGS. 5A–C, with the exception that, in place of handle coupling 80 of holder 70, holder 102,103 has a hole 106, as in FIG. 12A, or a post 108, as in FIG. 12B, adapted for attachment to a conventional handle for use in open heart surgery. Hole 106 and post 108 are designed to attach to such a conventional handle in an orientation in which at least a distal portion of the handle is perpendicular to the top surface 110, 111 and bottom surface 112, 113 of holder 102, 103 (and the plane of the annuloplasty ring held by the holder). The longitudinal axes of hole 106 and post 108 are thus perpendicular to surfaces 110, 111, 112, 113. A groove or channel 114, 115 extends around the lateral edge of each of holders 102, 103 and is configured to receive an annuloplasty ring.

Adaptors 104, 105, illustrated more clearly in FIGS. 13A–C and 14A–C, facilitate the attachment of a conventional angioplasty ring holder to delivery handle 10 of the invention. Adaptor 104 includes a downward-extending distal fitting 116 configured for insertion into a handle attachment hole in a holder like holder 102 of FIG. 12A. Adaptor 104 further includes a proximally-extending proximal fitting 118 for attachment to holder coupling 26 of delivery handle 10. Distal fitting 116 comprises a cylindrical member 120 with an annular groove 122 in which an O-ring 124 is disposed. Cylindrical member 120 may be inserted into hole 106 in holder 102 and is retained therein by O-ring 124. Alternatively, for annuloplasty ring holders having a threaded handle attachment hole, cylindrical member 120 may have external threads to couple to the threaded hole. In a preferred embodiment, proximal fitting 118 comprises a slot 126 having an open proximal end 128 through which holder coupling 26 is received and an open distal end 130 through which catch 44 may extend. As shown in FIG. 13C, the longitudinal axis of slot 126 is preferably perpendicular to the longitudinal axis of cylindrical member 120. However, as with holder 70 described above in connection with FIGS. 10 and 11, slot 126 may be at a variety of angles relative to cylindrical member 120 so long as the annuloplasty ring held on holder 102 may be positioned through an intercostal space without significant retraction of the adjacent ribs. Usually, slot 126 is between about −45° and +45°, and preferably −20° to +20°, relative to the longitudinal axis of cylindrical member 120.

Referring now to FIGS. 14A–14C, adaptor 105 comprises a distal fitting 132 and a proximal fitting 134. In this embodiment, distal fitting 132 is adapted to attach to post 108 on holder 103, and comprises a cylindrical aperture 136 for receiving post 108. Cylindrical aperture 136 may include an internal O-ring (not shown) or may be tapered so as to frictionally engage post 108. Alternatively, if post 108 is externally threaded, aperture 136 may include internal threads to retain post 108 therein. Proximal fitting 134 preferably comprises a slot 138 having an open proximal end 140 and an open distal end 142 so as to receive holder coupling 26 of delivery handle 10 as described above in connection with adaptor 104. Again, slot 138 is preferably perpendicular to the longitudinal axis of aperture 136, but it may be at various other angles depending upon the size and shape of holder 103 and the annuloplasty ring it is designed to carry.

While only two configurations of the adaptor and holder assembly of the invention are shown in FIGS. 12–14, it will be understood by those of ordinary skill in the art that various other configurations are possible to adapt virtually any of the annuloplasty ring holders currently available for attachment to delivery handle 10 of the invention. In most cases, this will simply require adapting the distal fitting of the adaptor for the particular handle attachment means utilized on the ring holder.

Figure 15:
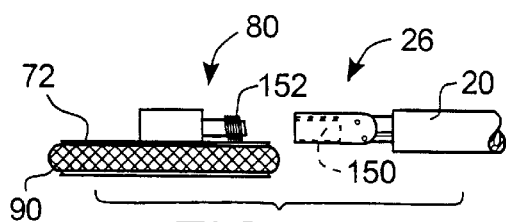
FIGS. 15–18, 19A and 20A are side views of an annuloplasty ring on a holder and a distal portion of a delivery handle in various alternative embodiments thereof.
Figure 16:
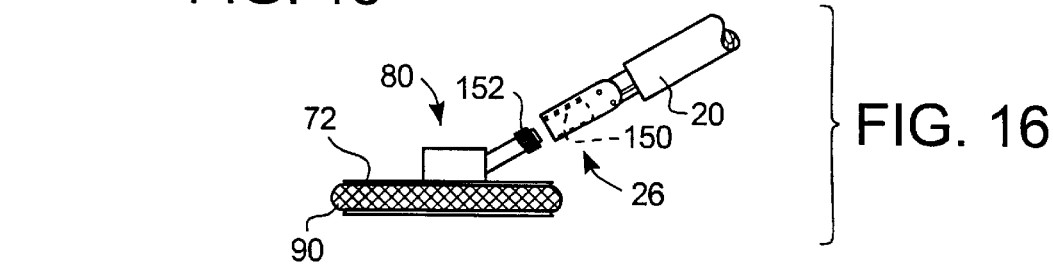
Figure 17:
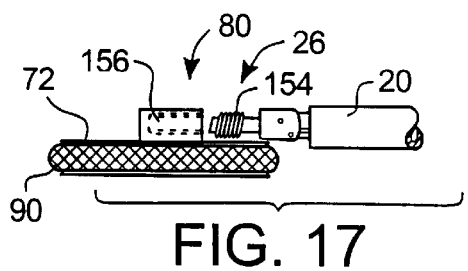
Figure 18:
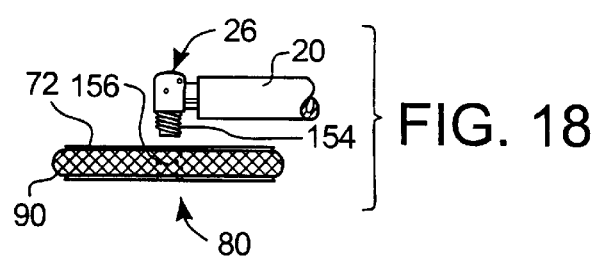

Although the foregoing embodiments of holder 70 and adaptors 104, 105 have been shown as having a handle coupling in the form of a slot for receiving tongue 34 of delivery handle 10, various other types of handle/holder couplings may also be utilized. Various exemplary embodiments are illustrated in FIGS. 15–20. In the embodiments of FIGS. 15 and 16, holder coupling 26 on delivery handle 10 comprises a threaded aperture 150, and handle coupling 80 on holder 70 comprises a threaded shank 152 which may be threaded into aperture 150. In FIG. 15, the longitudinal axis of threaded shank 152 is parallel to holder body 72, while in FIG. 16, the longitudinal axis of threaded shank 152 is disposed at an angle relative to holder body 72, preferably between −45° and +45°. In FIGS. 17 and 18, holder coupling 26 comprises a threaded shank 154, and handle coupling 80 comprises a threaded aperture 156. The longitudinal axis of threaded aperture 156 may be parallel to holder body 72 as in FIG. 17, or at an angle similar to threaded shank 152 of FIG. 16. Alternatively, the longitudinal axis of threaded aperture 156 may be perpendicular to holder body 72 as in FIG. 18, and threaded shank 154 may be mounted to shaft 20 so that the longitudinal axis of threaded shank 154 is perpendicular to shaft 20.

Figure 19A:
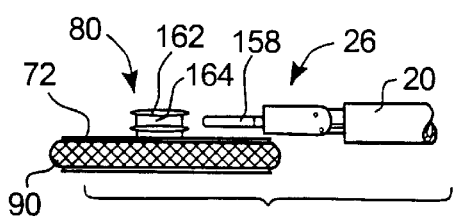
Figure 19B:
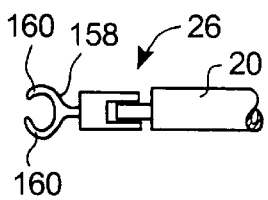
FIGS. 19B and 20B are top views of the distal portion of the delivery handle of FIGS. 19A and 20A, respectively.
Figure 20A:
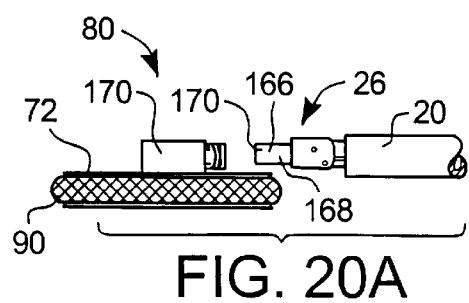
Figure 20B:
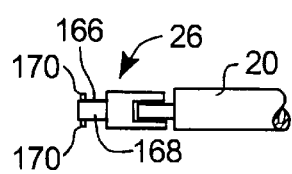

In the embodiment of FIGS. 19A–B, holder coupling 26 comprises a jaw 158 having a pair of resilient, arcuate jaw members 160 forming a C-shape. Handle coupling 80 comprises a cylindrical post 162 with an annular channel 164 formed therein which is configured to receive jaw 158. In this way, jaw 158 is attached to post 162 by sliding jaw members 160 around post 162 within annular channel 164. Jaw 158 is slightly undersized relative to post 162, such that jaw members 160 flex outwardly as they are inserted into annular channel 164 and exert an inward force on post 162 to maintain a tight grip thereon.

In still another embodiment, holder coupling 26 comprises a bayonet fitting 166 having a cylindrical body 168 and a pair of radially extending tabs 170. Handle coupling 80 comprises a cylindrical receptacle 172 having a pair of helical slots 174 in its sidewall for receiving tabs 170. In this way, bayonet fitting 166 may be inserted into receptacle 172 and twisted to form a tight attachment.

It should be understood that the above are only some of the possible configurations for holder coupling 26 and handle coupling 80, and should not be taken to limit the range of possible interconnections between holder 70 and delivery handle 10. In addition to those described above, other possible connection means include luer fittings, snap fittings, spring-loaded catches, magnetic attachments, movable jaws on delivery handle 10 for grasping holder 70, and various others. In addition, holder 70 may be permanently and non-removably attached to delivery handle 10.

Figure 21:
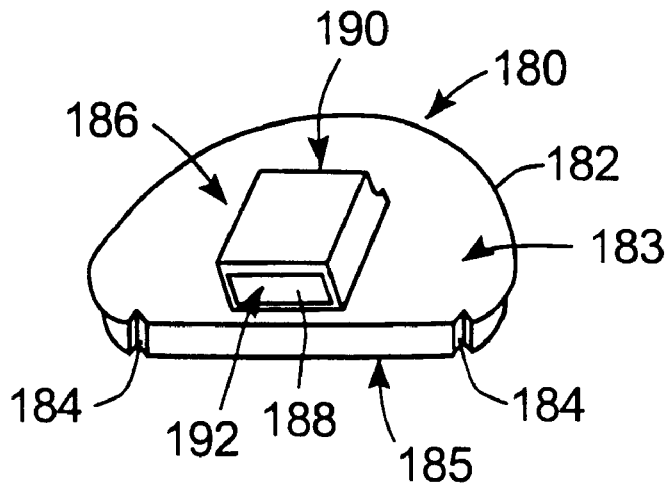
FIGS. 21 and 22 are perspective views of an annuloplasty ring sizing disk and sizing disk assembly, respectively, constructed in accordance with the principles of the invention.

In order to select an annuloplasty ring of the correct size for the valve being repaired, the native valve must be sized. Sizing disks may be used for this purpose. As will be described more fully below, sizing disks of various sizes are positioned adjacent the native valve to be repaired until a disk of the proper size is identified. An annuloplasty ring of a corresponding size is then selected for attachment around the native valve. A similar technique is used for sizing a native valve for replacement with a prosthetic valve. Advantageously, the present invention provides devices and methods for sizing a native valve which may be utilized through an intercostal port, without retraction or removal of ribs. FIG. 21 illustrates a preferred embodiment of a sizing disk according to the invention. Sizing disk 180 comprises a disk body 182 shaped similarly to the native valve annulus and having and having an upper face 183 and a lower face 185. Disk body 182 is preferably a transparent material such as polysulfone or polycarbonate such that the native valve is visible when the sizing disk is positioned in front of it. Two or more notches 184 or other markings may be disposed along a side of sizing disk 180 to facilitate measuring the spacing of the native valve trigones or commissures. Sizing disk 180 also includes a handle coupling 186 for attaching the sizing disk to delivery handle 10. Handle coupling 186 comprises, in a preferred embodiment, a slot 188 having an open proximal end 190 and an open distal end 192. Holder coupling 26 of delivery handle 10 is received into slot 188 through proximal end 190 and catch 44 extends out of slot 188 through distal end 192. Slot 188 is disposed at an angle relative to disk body 182 selected to allow sizing disk 180 to be introduced through an intercostal space using delivery handle 10 without retraction or removal of ribs. Usually the longitudinal axis of slot 188 is between −45° and +45°, and is preferably parallel to, upper and lower faces 183, 185 of disk body 182. With this configuration, sizing disk 180 may be attached to holder coupling 26 of delivery handle 10 and introduced through an intercostal port with disk body 182 generally parallel to the longitudinal axis of shaft 20. Once within the chest cavity, sizing disk 180 may be pivoted relative to shaft 20 into a perpendicular orientation such that the disk face is parallel to the native valve for the measurement thereof. Of course, like holder 70, handle coupling 186 may have a variety of other configurations, such as those of handle coupling 80 described above in connection with FIGS. 15–20.

Figure 22:
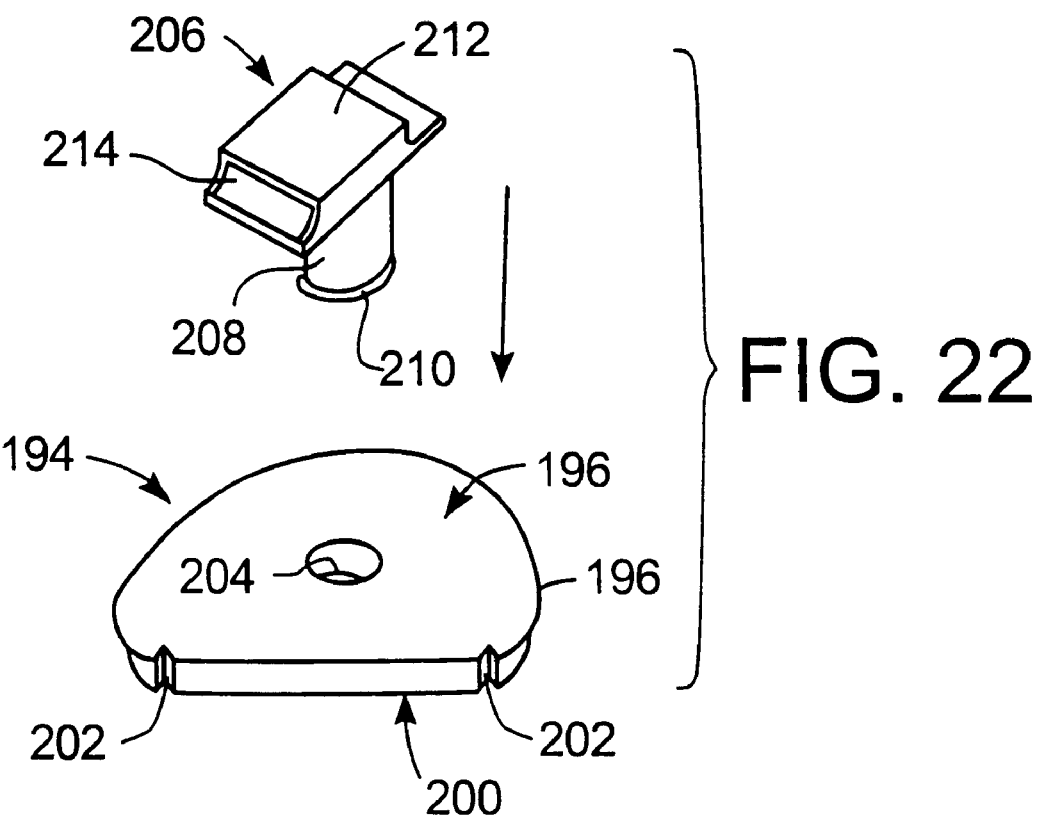

A second embodiment of a native valve sizer according to the invention is illustrated in FIG. 22. In this embodiment, sizing disk 194 may be any of a variety of commercially-available sizing disks for use with the annuloplasty rings currently used in open heart surgery. Sizing disk 194 has a disk body 196 with an upper face 198 and a lower face 200. Two or more notches 202 or other markings may be provided on a side of disk body 196 for measurement of a native valve leaflet. A hole 204 is disposed in a central region of disk body 196 for attachment of the sizing disk to a conventional handle for use in open heart surgery. An adaptor 206 is further provided for attaching sizing disk 194 to delivery handle 10. In a preferred embodiment, adaptor 206 has a configuration like adaptor 104 described above in connection with FIGS. 12–14. Adaptor 206 has a cylindrical member 208 extending downwardly and configured for insertion into hole 204. Cylindrical member 208 may include an O-ring 210 for securing the cylindrical member within hole 204. Alternatively, if hole 204 has internal threads, cylindrical member 208 may have external threads.

Other types of interconnections may also be used, such as a cylindrical aperture on adaptor 206 designed to receive a post or shank on sizing disk 194, like that described above in connection with holder 103 of FIG. 12B. Adaptor 206 also has a handle coupling 212, which preferably comprises a slot 214 for receiving holder coupling 26 of delivery handle 10. Slot 214 is preferably perpendicular to the longitudinal axis of cylindrical member 208, so as to be parallel to the upper and lower faces 198, 200 of sizing disk 194 when connected to it. Slot 214 may be disposed at other angles as well, so long as sizing disk 194, when connected to adaptor 206 and delivery handle 10, may be introduced through an intercostal port without removing or significantly retracting the ribs. As with sizing disk 180 of FIG. 21, various other handle coupling configurations may also be utilized on adaptor 206.

Figure 23:
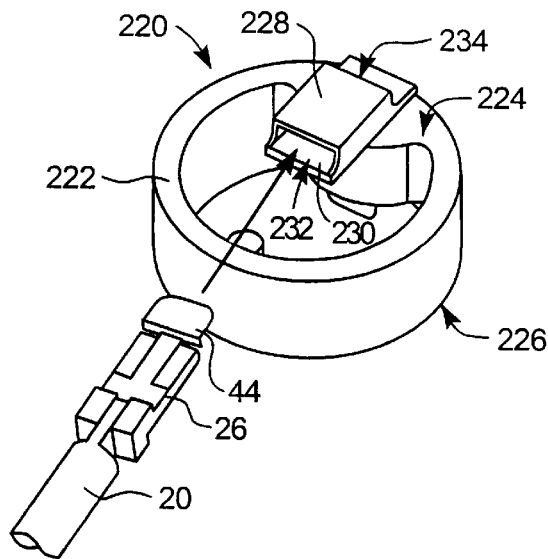
FIG. 23 is a perspective view of a replacement valve sizing disk constructed according to the invention.

For cases in which valve repair is inappropriate, the invention also provides devices and methods for sizing a native valve which is to be replaced with a prosthetic valve. A replacement valve sizing disk according to the invention is illustrated in FIG. 23. Valve sizing disk 220 includes a disk body 222 having an upper face 224 and a lower face 226. Disk body 222 has a shape corresponding to that of the prosthetic valve to be used for replacing the native valve, and is usually circular. A handle coupling 228 is mounted to upper face 224. Handle coupling 228 preferably comprises a slot 230 configured to receive holder coupling 26 of delivery handle 10. Slot 230 has an open proximal end 232 through which coupling member 26 is received, and an open distal end 234 through which catch 44 may extend. The longitudinal axis of slot 230 is preferably parallel to upper and lower faces 224, 226 of disk body 222, but may be at other angles, usually between about −45° and +45°, so long as sizing disk 220, when attached to coupling means 26 of delivery handle 10, may be introduced through an intercostal space without retraction or removal of ribs. A multitude of alternative configurations for handle coupling 228 are also possible, including those described above in connection with FIGS. 15–20.

Figure 24A:
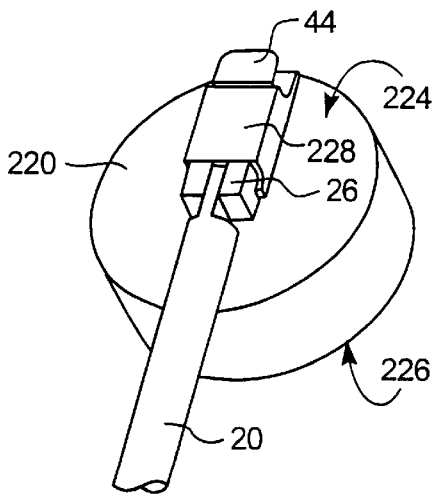
FIGS. 24A–24B are perspective views of the sizing disk of FIG. 23 attached to the delivery handle of FIG. 1, in two alternative orientations.
Figure 24B:
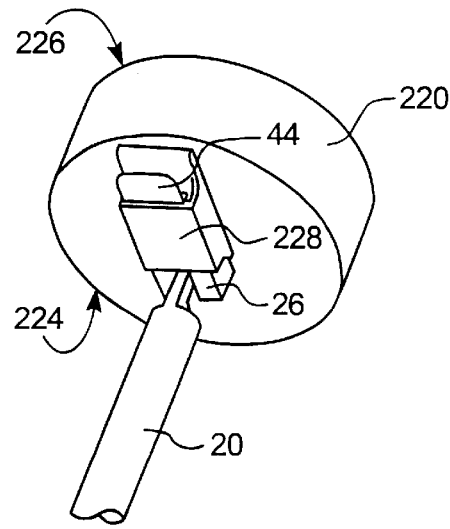

When sizing disk 220 is attached to delivery handle 10 and positioned in the orientation of FIG. 24A, upper and lower faces 224, 226 are parallel to the longitudinal axis of shaft 20, and the combined profile of sizing disk 220 and shaft 20 is minimized to facilitate introduction through an intercostal port. Once positioned within the chest cavity, sizing disk 220 may be pivoted into the orientation of FIG. 24B, wherein faces 224, 226 are generally perpendicular to the longitudinal axis of shaft 20. In this orientation, sizing disk 220 may be positioned so that lower face 226 is facing the native valve to allow sizing disk 220 to be pushed in and out of and/or positioned within the native valve annulus to compare the native annulus size to the sizing disk size. This process is repeated using sizing disks of various diameters until the proper size is determined.

Figure 25:
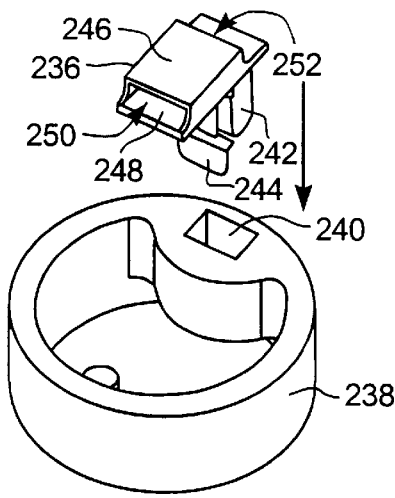
FIG. 25 is a perspective view of a sizing disk assembly constructed according to the invention.

FIG. 25 illustrates an alternative embodiment of a sizing disk assembly according to the invention, wherein an adaptor 236 is utilized for attaching a conventional sizing disk 238 to delivery handle 10. Sizing disk 238 may be any of a variety of sizing disks currently in use in open heart valve replacement surgeries, and has a shape corresponding to the shape of the prosthetic valve to be used for the replacement. Sizing disk 238 has a hole 240 of rectangular cross-section suitable for attachment to a conventional handle utilized in open heart surgery. Adaptor 236 includes a rectangular tongue 242 configured for insertion into hole 240. A leaf spring catch 244 similar to catch 44 on delivery handle 10 is provided on tongue 242 to retain it within hole 240. Alternatively, sizing disk 238 may have a post or shank extending upwardly from it, in which case cylindrical member 242 may have an internal aperture for receiving the post or shank. Adaptor 236 further includes a handle coupling 246, which preferably comprises a slot 248 having an open proximal end 250 for receiving holder coupling 26, and an open distal end 252 through which catch 44 may extend. The longitudinal axis of slot 248 is preferably perpendicular to the longitudinal axis of tongue 242 so that, when adaptor 236 is connected to sizing disk 238, the slot is generally parallel to the face of the sizing disk. In this way, coupling member 26 of delivery handle 10 may be inserted through slot 248 and sizing disk may be oriented so that it is parallel to the longitudinal axis of shaft 20, thereby having a minimum profile for introduction through an intercostal port.

Once the native valve has been sized for replacement, delivery handle 10 of the invention may also be used to deliver the replacement valve into the heart for attachment at the native valve position, using techniques described in detail below. In order to facilitate introducing the replacement valve through an intercostal space without retracting or removing ribs, the invention provides a replacement valve holder having an extremely small profile and adapted for attachment to delivery handle 10. A preferred embodiment of a valve holder according to the invention is shown in FIGS. 26A–26C. Valve holder 260 is adapted for holding a mechanical bileaflet valve prosthesis as shown in FIG. 28, which may be, for example, a bileaflet mitral or aortic valve prosthesis available from St. Jude Medical, Inc. of St. Paul, Minn., CarboMedics, Inc. of Austin, Tex., or Sorin Biomedica of Saluggia, Italy. In the example of FIG. 28, valve prosthesis 262 has an annular frame 264 and a sewing ring 266 attached to frame 264 for attachment to an interior wall of the heart at the native valve position. Sewing ring 266 is covered by a fabric or mesh of e.g. Dacron to allow the prosthesis to be sutured to the heart tissue. A pair of parallel uprights 268 extend axially upward from frame 264. A pair of leaflets 270 having curved outer edges 272 and straight inner edges 274 are pivotably mounted to uprights 268. Leaflets 270 are movable between a closed position, in which straight inner edges 274 are contacting each other and curved outer edges are contacting the inner wall of annular frame 264, and an open position in which leaflets are spaced apart from each other and from annular frame 264. Frame 264, uprights 268 and leaflets 270 are made of a rigid biocompatible polymer, metal or graphite coated with a thrombolytic material such as pyrolytic carbon.

Referring again to FIGS. 26A–26C, valve holder 260 comprises a distal piece 276 and a proximal piece 278 pivotably coupled together by two transverse pins 280, allowing distal piece 276 to pivot about a transverse axis relative to proximal piece 278, as shown in FIG. 27. Distal piece 276 has a top portion 282 which is bifurcated into two parallel side sections 282A, 282B. Proximal piece 278 has a single top portion 284 disposed between side sections 282A, 282B. Pins 280 extend through side sections 282A, 282B and into top portion 284. An axial slot 286 extends through top portion 284 in an axial direction, and is configured to receive holder coupling 26 on delivery handle 10. Axial slot 286 has an open proximal end 288 through which tongue 34 is inserted and an open distal end 290 through which catch 44 may extend. A pair of transverse suture holes 287, 289 extend through sides sections 282A, 282B and through top portion 284 for tying a retention suture, as described below. Distal piece 276 has a distal leg 292 extending downwardly from top portion 282 and having a distally-facing annular channel 294 for receiving a portion of annular frame 264 of valve prosthesis 262. Proximal piece 278 has a proximal leg 296 extending downwardly from top portion 284 and having a proximally-facing annular channel 298 for receiving a portion of annular frame 264. When legs 292, 296 are pivoted into the position of FIG. 27, valve prosthesis 262 may be positioned over the legs, which are disposed between each valve leaflet 270 and annular frame 264. Legs 292, 296 may then be pivoted outwardly to seat annular frame 264 in channels 294, 298, as shown in FIG. 29. A suture 300 may then be tied through suture holes 287, 289 to maintain distal piece 276 and proximal piece 278 in an outward position to retain valve prosthesis 262 thereon.

Figure 30A:
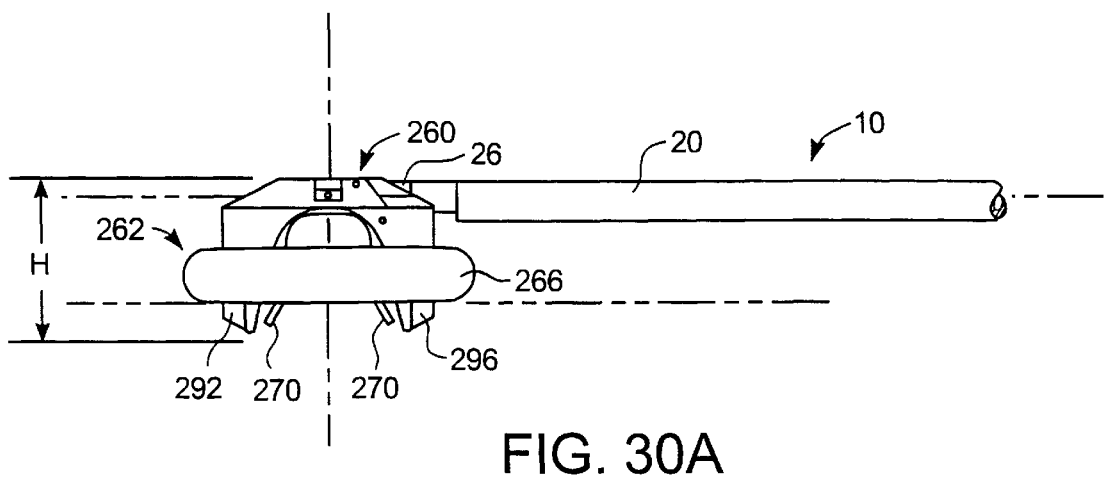
FIGS. 30A–30B are front views of the holder and prosthetic valve of FIG. 29 attached to the delivery handle of FIG. 1, in two alternative orientations.
Figure 30B:
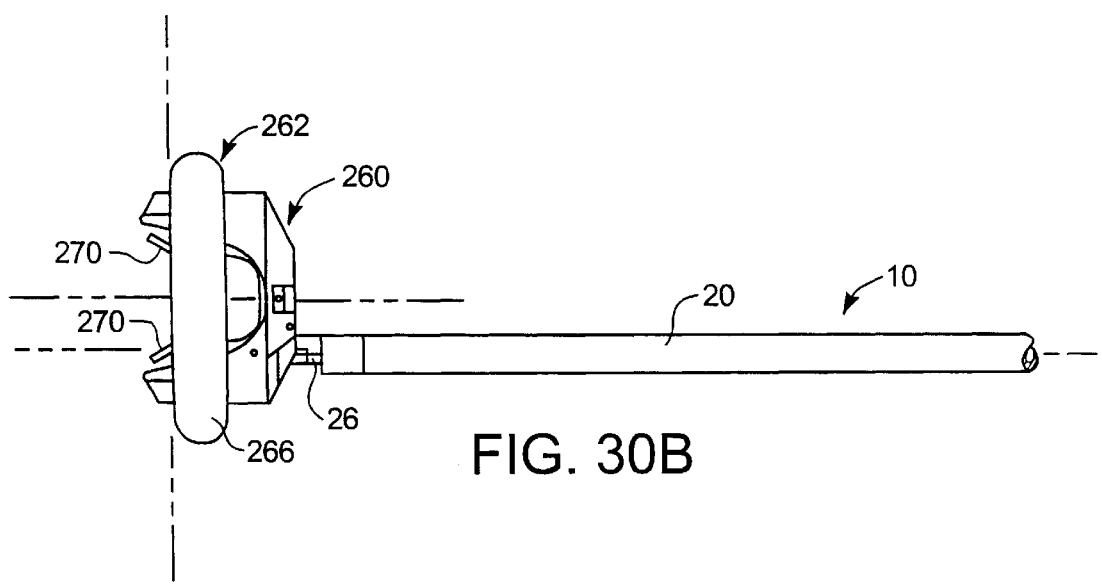

FIGS. 30A–30B illustrate valve prosthesis 262 mounted to holder 260, which is attached to holder coupling 26 of delivery handle 10. In the introduction position of FIG. 30A, holder coupling 26 is aligned with the longitudinal axis of shaft 20, such that the plane containing the lower surface of sewing ring 266 is generally parallel to the longitudinal axis of shaft 20. Alternatively stated, the central longitudinal axis of valve prosthesis 262 is generally perpendicular to the longitudinal axis of shaft 20. In this position, the overall height H of holder 260, valve prosthesis 262, and shaft 20 is minimized to facilitate introduction through an intercostal port, with height H usually being less than about 30 mm and preferably less than about 25 mm. Of course, some deviation from this orientation may be possible without hindering introduction through the intercostal port. For example, depending upon the size of the valve prosthesis relative to the width of the intercostal space, valve prosthesis 286 may be positioned as much as about +/−45° from the position of FIG. 30A during introduction. Once valve prosthesis 262 has been introduced through the intercostal port, it may be pivoted into an orientation suitable for attachment at the native valve position within the heart. In the attachment orientation, the central longitudinal axis of valve prosthesis 262 will preferably be parallel to the longitudinal axis of shaft 20, such that the lower surface of sewing ring 266 is facing and parallel to the interior wall of the heart to which the valve will be attached. A variety of other angular orientations may also be used where a nonperpendicular approach to the valve has been taken, or in other appropriate circumstances. Advantageously, delivery handle 10 allows the valve prosthesis to be pivoted into a wide range of angular orientations according to the needs of each particular case.

FIG. 30A also illustrates an important advantage of holder 260 of the invention. It may be seen that distal leg 292 and proximal leg 296 extend below the lower ends of valve leaflets 270. In this way, when valve prosthesis 262 is mounted to holder 260, leaflets 270 are protected from damage during introduction and placement.

Figure 31:
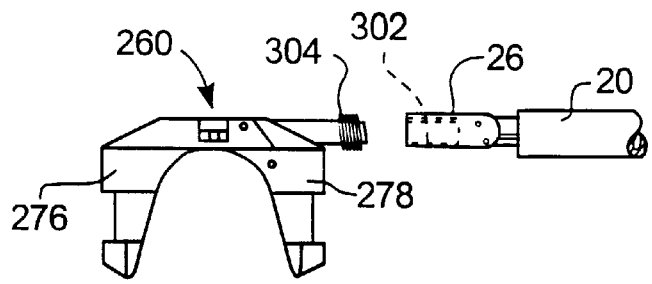
FIGS. 31–34 are side views of a prosthetic valve holder and a distal portion of a delivery handle in various alternative embodiments thereof.
Figure 32:
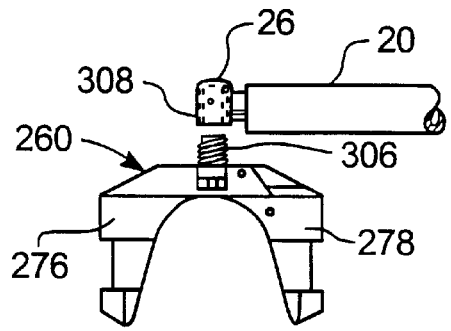
Figure 33:
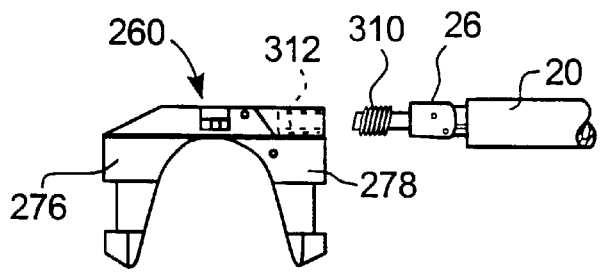
Figure 34:
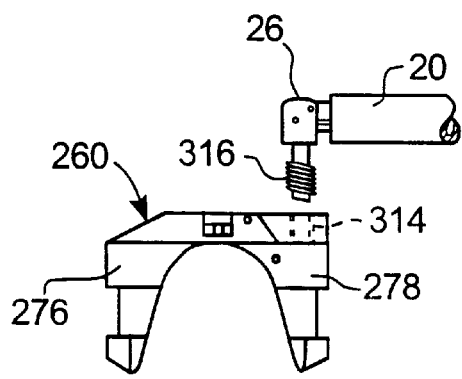

In the embodiment of FIGS. 26–30, valve holder 260 is attached to delivery handle 10 by means of axial slot 286 which receives holder coupling 26 on the handle. However, it will be understood to those of ordinary skill in the art that a variety of other handle attachment means may be used on the valve holder of the invention. Four exemplary alternative handle attachment means are shown in FIGS. 31–34. In FIG. 31, holder coupling 26 on handle 10 comprises an internally-threaded aperture 302, and holder 260 is attached to handle 10 by a threaded shank 304 extending proximally from proximal piece 278 which may be threaded into aperture 302. Shank 304 may be at a variety of angles relative to holder 260, but is preferably perpendicular to the longitudinal axis of the holder. In FIG. 32, a threaded shank 306 on holder 260 on the top of proximal piece 278 is generally parallel to the longitudinal axis of holder 260 for connection to a laterally-oriented internally-threaded aperture 308 on holder coupling 26. In FIG. 33, a threaded shank 310 on holder coupling 26 couples to a threaded hole 312 in holder 260 which is perpendicular to the longitudinal axis of the holder. In FIG. 34, a threaded hole 314 is parallel to the longitudinal axis of the holder and connects to a laterally oriented threaded shank 316 on holder coupling 26. Various other handle connection mechanisms are also possible, including bayonet fittings, luer locks, spring-loaded catches, holder-gripping jaws on handle 10, and permanent, nondetachable linkages. The particular type of attachment means is not critical, so long as valve holder 260 may be connected to delivery handle 10 in an orientation which allows valve prosthesis 262 to be held on holder 260 and introduced through an intercostal port without removing or retracting the ribs.

In addition to the bileaflet valve prosthesis illustrated in FIG. 28, the prosthesis holder and delivery system may also be adapted for use with a variety of other types of prosthetic valves, both mechanical and bioprosthetic. Various types of prosthetic valves useful with the invention are described in Jamieson, "Modem Cardiac Valve Devices—Bioprostheses and Mechanical Prostheses: State of the Art,"*J. Card. Surg.* 8:89–98 (1993). Mechanical valves which may be used include the caged-ball type such as the Starr-Edwards™ valve (Baxter Healthcare Corp., Edwards CVS Division, Irvine, Calif.), the tilting disk type such as the Medtronic-Hall™ valve (Medtronic, Inc., Minneapolis, Minn.), the Bjork-Shiley Monostrut™ valve (Shiley, Inc., Irvine, Calif.), the Omniscience™ valve (Omniscience Medical, Inc., Grove Heights, Minn.), as well as the bileaflet type such as the Baxter Duromedics™ Valve (Baxter Healthcare Corp., Edwards CVS Division, Irvine, Calif.), St. Jude valve (St. Jude Medical Inc., St. Paul, Minn.), Carbomedics valve (CarboMedics, Inc., Austin, Tex.), or Sorin valve (Sorin Biomedica, Saluggia, Italy). Bioprosthetic valves which may be placed using the devices and techniques of the invention include porcine aortic valves such as the Hancock II™ bioprosthesis (Medtronic, Inc., Minneapolis Minn.), the Carpentier-Edwards™ supraannular bioprosthesis (Baxter Healthcare Corp., Edwards CVS Division, Irvine, Calif.), the Carpentier-Edwards™ stentless bioprosthesis (Baxter Healthcare Corp., Edwards CVS Division, Irvine, Calif.), the St. Jude Bioimplant™ bioprosthesis (St. Jude Medical Inc., St. Paul, Minn.), or the Medtronic Intact™ bioprosthesis (Medtronic, Inc., Minneapolis, Minn.). Other valves which may be used include the Mitroflow™ bioprosthesis (Mitroflow International, Inc., Richmond, British Columbia, Canada), and the Carpentier-Edwards™ pericardial bioprosthesis (Baxter Healthcare Corp., Edwards CVS Division, Irvine, Calif.). The invention also facilitates valve replacement with homografts and allografts, polymeric valves, and a variety of mechanical and bioprosthetic valves not specifically listed here.

The methods of repairing and replacing a diseased heart valve according to the invention will now be described with reference to FIGS. 35–46. The patient must first be prepared for surgery by inducing general anesthesia, establishing cardiopulmonary bypass, and inducing cardioplegic arrest. Devices and techniques for inducing cardioplegic and establishing cardiopulmonary bypass which may be used in conjunction with the method of the present invention are described in co-pending application Ser. Nos. 08/282,192, filed Jul. 28, 1994, 08/159,815, filed Nov. 30, 1993, and 08/173,899, filed Dec. 27, 1993, which are incorporated herein by reference. As described in those applications, after general anesthesia has been induced, cardiopulmonary bypass is initiated by placing a venous cannula in a major peripheral vein such as a femoral vein, and placing an arterial cannula in a major peripheral artery such a femoral artery. The venous and arterial cannulae are connected to a cardiopulmonary bypass system, which includes an oxygenator for oxygenating blood withdrawn from the patient through the venous cannula, a filter for removing emboli from the blood, and a pump for returning the blood to the patient's arterial system through the arterial cannula.

With cardiopulmonary bypass established, cardioplegic arrest may be induced. Although conventional, open-chest external aortic cross clamping and aortic cannulation through the aortic wall may be utilized, closed-chest cardioplegia techniques are preferred. As described in the forementioned copending applications, cardioplegia may be induced on a closed-chest patient by introducing an aortic catheter into a femoral artery or other major peripheral artery, transluminally positioning the distal end of the aortic catheter in the ascending aorta, and expanding an expandable member such as a balloon on the distal end of the aortic catheter to occlude the ascending aortic lumen between the coronary ostia and the brachiocephalic artery. A cardioplegic agent, preferably comprising a potassium chloride solution mixed with blood, is then delivered through a lumen of the aortic catheter into the ascending aorta, where the cardioplegic fluid flows into the coronary arteries, perfusing the myocardium and arresting cardiac function. A venting catheter may also introduced into the right side of the heart or into the pulmonary artery from a peripheral vein, as described in copending application Ser. No. 08/415,238, filed Mar. 30, 1995, which is incorporated herein by reference. In addition, a retrograde cardioplegia catheter may be introduced from another peripheral vein into the coronary sinus for delivering cardioplegic fluid into the coronary sinus under sufficient pressure to flow in a retrograde manner through the coronary veins to perfuse the myocardium, as described in copending application Ser. No. 08/372,741, filed Jan. 12, 1995, which is incorporated herein by reference.

As an alternative to these endovascular techniques, cardioplegic arrest may be induced by occluding the ascending aorta with a thoracoscopic cross-clamp positioned externally on the aorta through an intercostal port in the anterior chest. Cardioplegic fluid may then be delivered upstream of the clamp with a cannula intraluminally positioned in the aorta from a peripheral artery, or by penetrating the aortic wall with a cannula introduced thoracoscopically. Such techniques are described in copendig application Ser No. 08/173,899, filed Dec. 27, 1993, which has been incorporated herein by reference.

In order to obtain access to the heart from the right lateral side of the chest, the right lung must be collapsed. This may be accomplished by inserting an endotracheal tube into the right main stem bronchus and applying a vacuum so as to deflate the lung.

Figure 35:
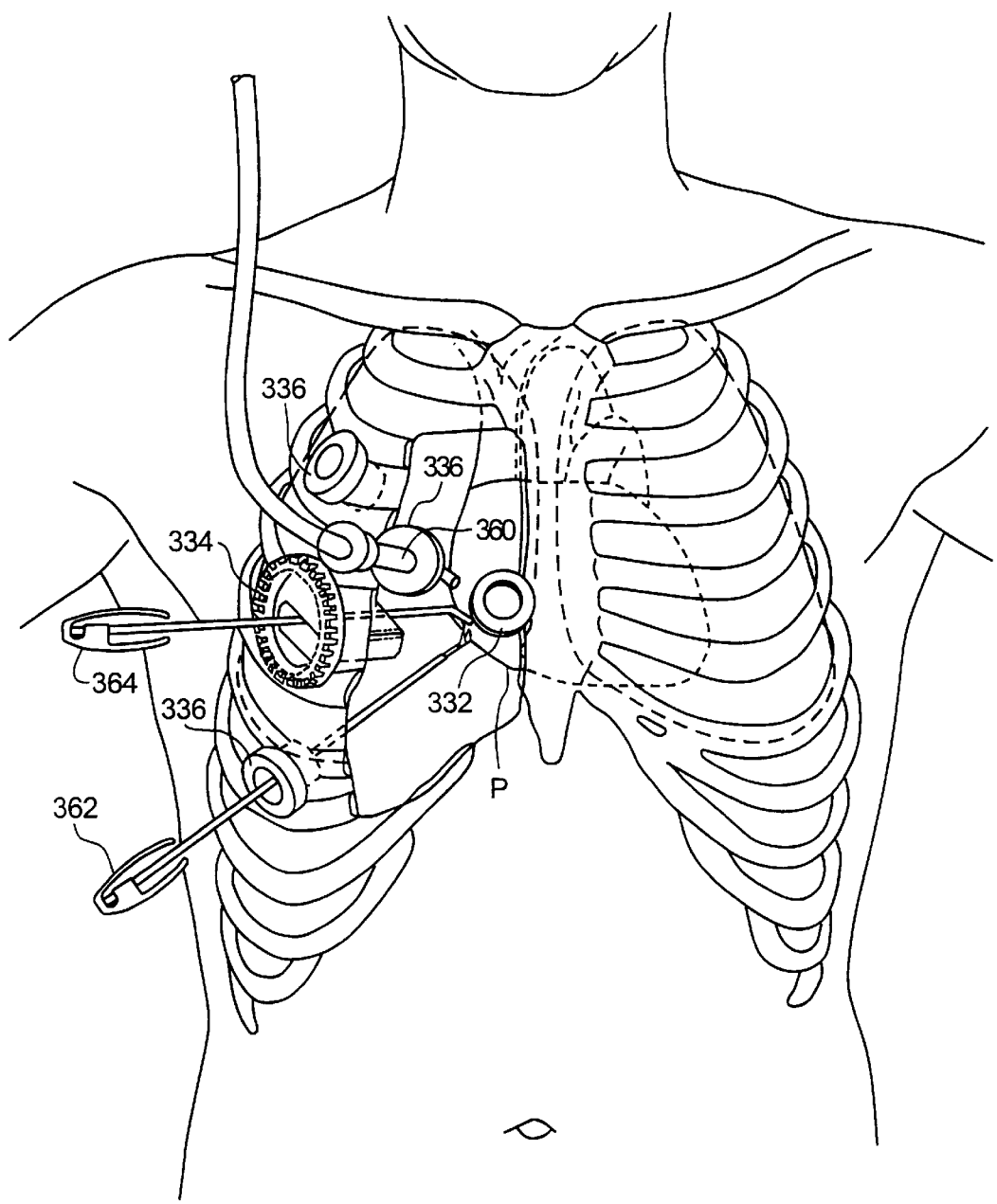
FIG. 35 is an anterior partially cut-away view of a patient's chest illustrating forming an opening in the pericardium according to a cardiac valve treatment method of the invention.
Figure 36D:
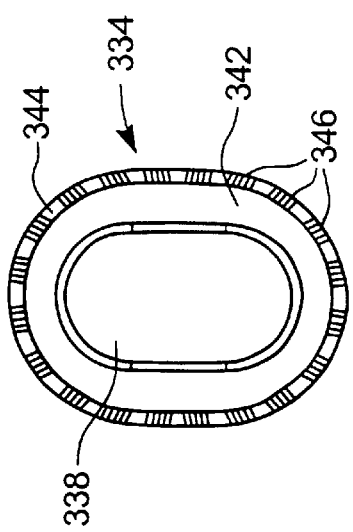
FIGS. 36A–36D are perspective, side, front and top views, respectively, of an oval port constructed in accordance with the principles of the invention.
Figure 36C:
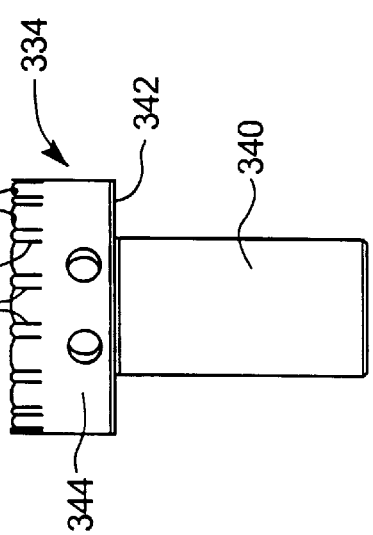
Figure 36B:
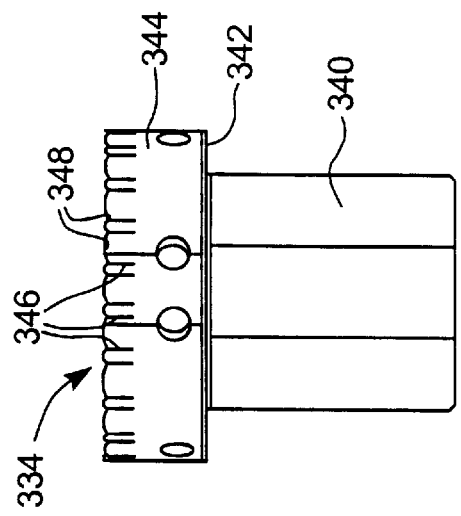
Figure 36A:
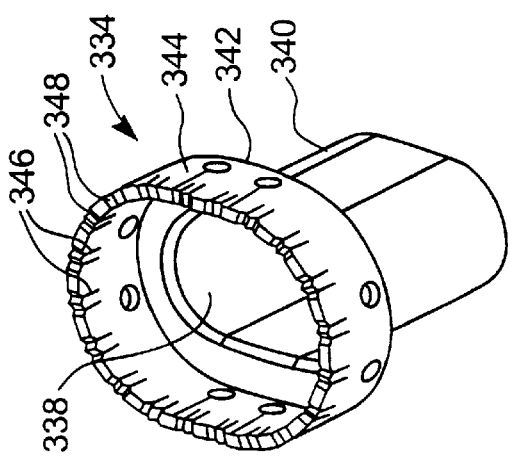

With cardiac function arrested and the patient's circulation supported by extracorporeal cardiopulmonary bypass, the patient is ready for the valve repair or replacement procedure. Referring to FIG. 35, a number of percutaneous cannulae, hereinafter referred to as "ports," are positioned in the anterior chest and right lateral chest to provide access into the chest cavity. In most cases, 3 to 5 ports are required, including a retraction port 332 located in the anterior chest over the right lateral wall of the right atrium, an oval port 334 located in the right lateral chest in the second, third, fourth, fifth or sixth intercostal space, and at least one instrument port 336 in the right lateral chest or anterior chest for introduction of instruments or visualization devices. Retraction port 332 and instrument ports 336 are configured for placement within an intercostal space without requiring retraction of the ribs, and are usually 5–12 mm in diameter. To introduce the ports, a small puncture or incision is made in the intercostal space at the desired location, and, with an obturator positioned in the lumen of the ports, they are advanced through the puncture or incision.

Oval port 334, illustrated in FIG. 36A–36D, is also configured for placement within an intercostal space without retraction of ribs, and has a width of less than about 30 mm, and preferably less than about 25 mm. Oval port 334 has a percutaneous tube 340 having a flange 342 at its proximal end to engage the outside of the chest when the oval port is introduced. A plurality of tie-down holes 343 are provided in flange 342 to facilitate securing oval port 334 to the patient by means of sutures or other tie-down means passed through holes 343. Percutaneous tube 340 has a length sufficient to extend from outside of the chest, through the intercostal space, and into the chest cavity just beyond the interior of the chest wall, the length typically being in the range of 30–50 mm. Percutaneous tube 340 has an inner lumen 338 with shape and dimensions selected to allow an annuloplasty ring or replacement valve on a holder to be introduced through it using delivery handle 10. Inner lumen 338 usually has a width of about 10–30 mm, and preferably 15–25 mm, and a height of about 25–75 mm, preferably 30–50 mm. The exact width and height will be determined by the width (or diameter) and height of the particular annuloplasty ring or replacement valve and holder being used in the procedure. It is usually desirable to begin the procedure with an oval port 334 of the minimum size necessary to assess the condition of the native valve and to allow introduction of valve sizing disks. For example, an oval port 334 having a width of about 15–°mm may be used initially. When the size of the annuloplasty ring or prosthetic valve to be used has been selected, the smaller oval port may be replaced, if necessary, with a larger oval port to accommodate the prosthesis.

Oval port 334 may also include a suture organizing ring 344 attached to flange 342 so as to surround inner lumen 338. Organizing ring 344 has a plurality of circumferentially-spaced radial slots 346 in which a suture thread may be received and retained by friction. Slots 346 have tapered upper ends 348 to allow a suture thread to be easily guided into the slot. Suture organizing ring 344 allows sutures placed in the heart for attachment of a prosthesis to be drawn through inner lumen 338 and temporarily placed in slots 346 so as to keep the sutures individually separated and untangled, as described more fully below.

Figure 37B:
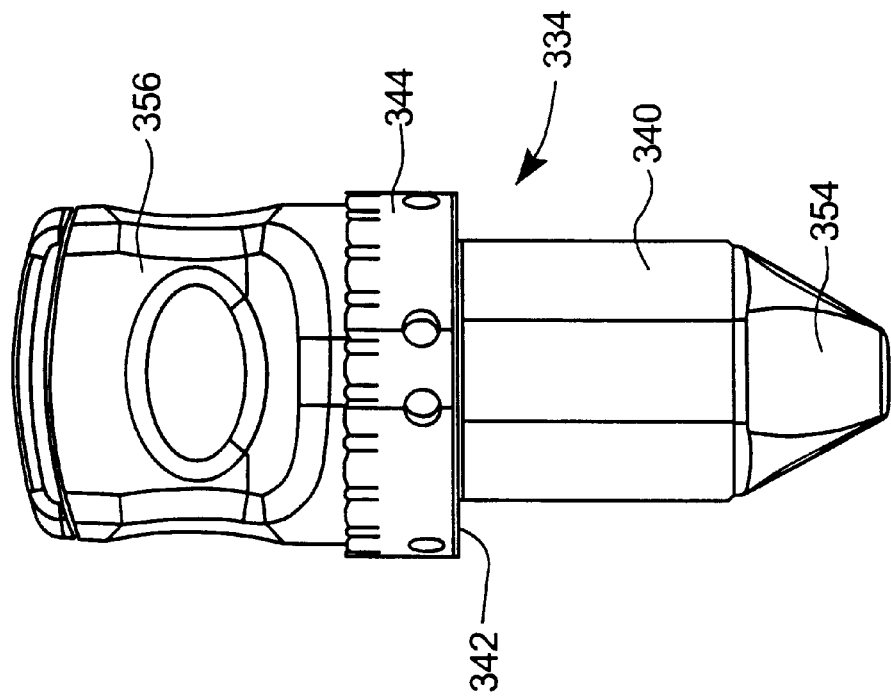
FIG. 37B is a side view of the obturator of FIG. 37A positioned in an inner lumen of the oval port of FIGS. 36A–36D.
Figure 37A:
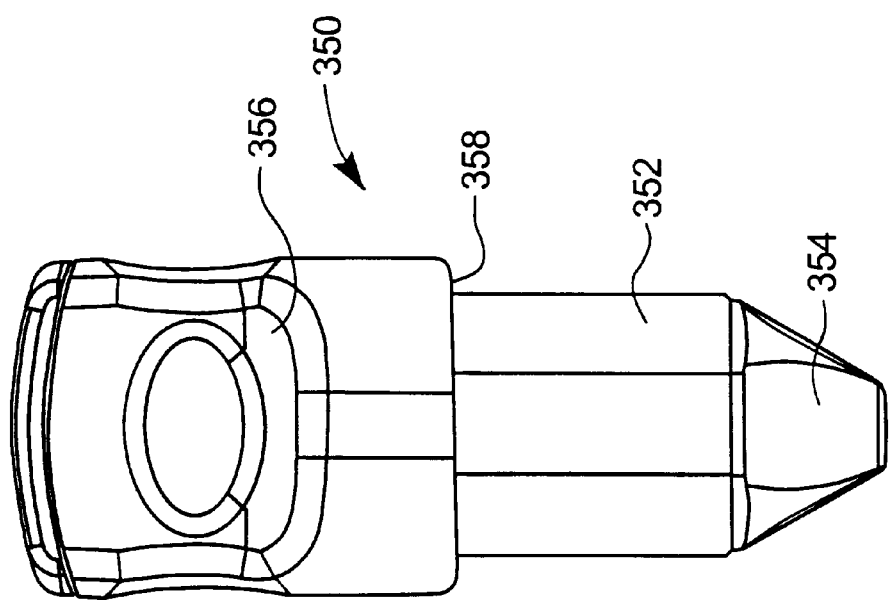
FIG. 37A is a side view of an obturator for the oval port of FIGS. 36A–36D.

In order to facilitate introducing oval port 334 through a puncture or small incision between the ribs, an obturator 350 may be slidably inserted into inner lumen 338, as illustrated in FIGS. 37A–B. Obturator 350 includes an oval shaft 352 positionable within inner lumen 338 and a tapered or pointed distal end 354 which extends distally of the distal end of percutaneous tube 340. A handle 356 is attached to the proximal end of oval shaft 352 and has a distal face 358 for engaging flange 342 on oval port 334. Handle 356 has shape and dimensions suitable for grasping in the hand of the user and applying a distally-directed force for percutaneous introduction. Once oval port 334 has been introduced through an intercostal space, obturator 350 is removed from inner lumen 338.

In addition to the oval configuration shown, oval port 334 may have an inner lumen of various other shapes, including race-track, rectangular, trapezoidal, elliptical or circular. Alternatively, oval port 334 may be made of a flexible or deformable material to allow it to be shaped by the user or to conform to the shape of the intercostal space. In addition, other means of tissue retraction may be used in place of oval port 334, such as a 3-sided channel-shaped member, or a wound retractor having a pair of adjustable parallel blades which can be placed in an intercostal incision and used to create a space by widening the distance between the blades. All of these may fall within the scope of the invention to the extent they facilitate introduction of a prosthetic annuloplasty ring or valve through an intercostal space without significant retraction or removal of the ribs or sternum.

Referring again to FIG. 35, with ports 332, 334, 336 in position, surgery within the chest cavity may begin. Much, if not all of the procedure may be carried out under direct vision by illuminating the chest cavity with a light source or light guide positioned in an instrument port or in the oval port and looking through the inner lumen of oval port 334 or through one of the instrument ports. Head-mounted surgical loupes specially designed for looking through a small incision or cannula may be utilized to facilitate direct vision through a port, such as the devices described in U.S. Pat. Nos. 4,836,188, 4,196,966, and 4,807,987, which are incorporated herein by reference. A fiberoptic bundle may also be attached to or embedded in the wall of one of instrument ports 336 or in percutaneous tube 340 of oval port 334 to transmit light into the chest from a light source outside the chest, in the manner disclosed in copending application Ser. No. 08/227,366, filed Apr. 13, 1994, which is incorporated herein by reference. In most cases, however, it will be desirable to introduce a thoracoscope 360 through an instrument port 336 to provide additional illumination and visualization of the chest cavity, preferably by means of a video camera mounted to thoracoscope 360 which transmits a video image to a monitor (not shown in FIG. 35). Thoracoscope 360 may comprise a rigid thoracoscope with a straight end or an angled end such as those available from, for example, Olympus Corp., Medical Instruments Division, Lake Success, N.Y. Alternatively, a thoracoscope with an articulated end steerable by means of an actuator at the proximal end of the device may be used, such as the Welch Allyn DistalVu™ (formerly Baxter DistalCam™ 360), available from Welch Allyn, Inc., of Skaneateles Falls, N.Y.

Thoracoscopic surgical instruments are then introduced in order to form an opening in the pericardium, which surrounds the heart. If the right lung is not sufficiently collapsed, atraumatic retraction instruments may be introduced through one of the ports to push the lung posteriorly such that the pericardium is visible by looking through oval port 334 or through one of instrument ports 336. Thoracoscopic scissors 362 and graspers 364 are then introduced through oval port 334 or instrument port 336 and used to cut an opening in the pericardium P. Suitable thoracoscopic instruments for use in the method of the invention are described in copending application Ser. Nos. 08/281,962, filed Jul. 28, 1994, and Ser. No. 08/194, 946, filed Feb. 11, 1994, which are incorporated herein by reference.

Figure 38:
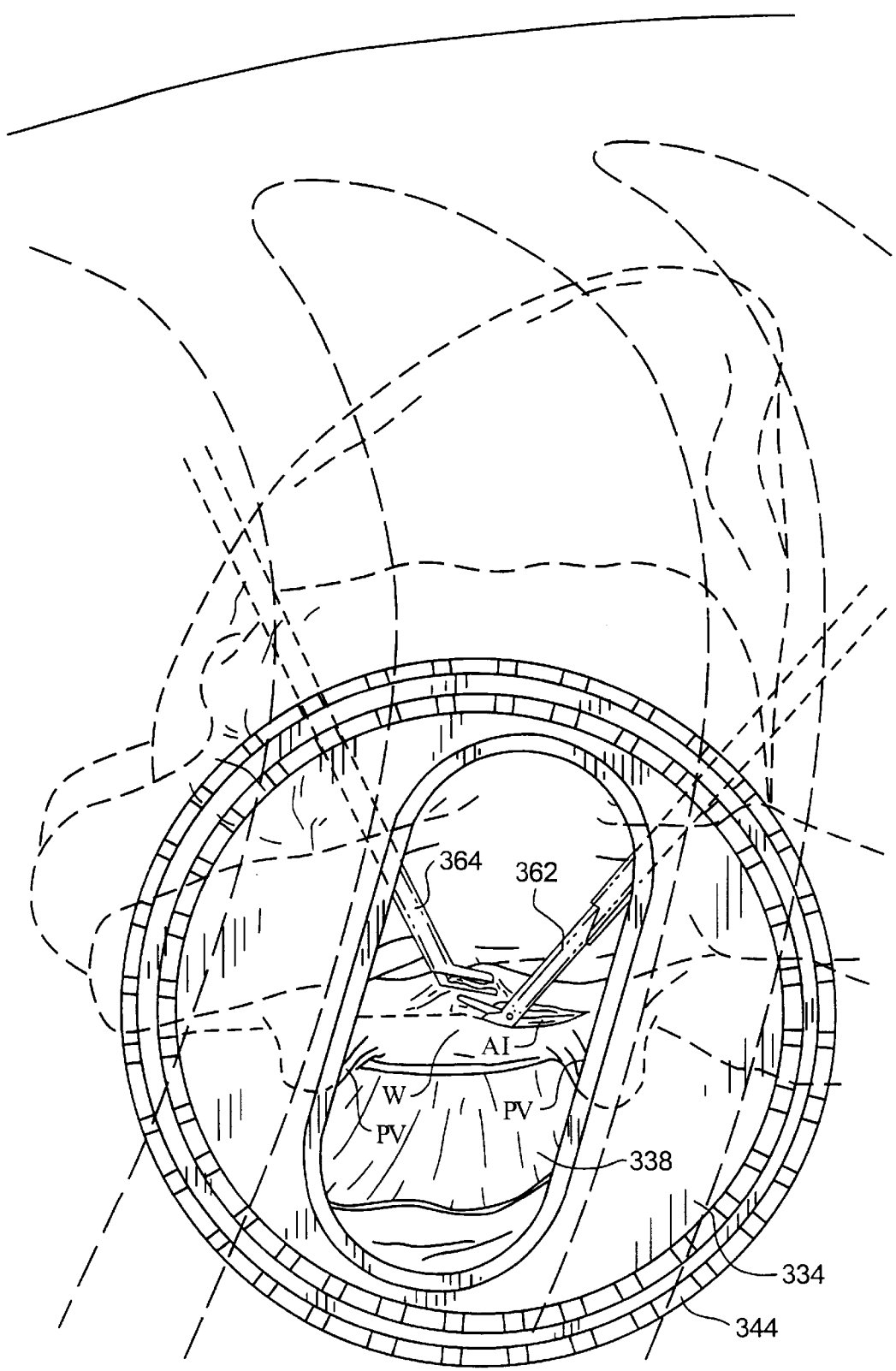
FIG. 38 is an elevational view through the oval port of FIGS. 36A–36D positioned in a right lateral location of a patient's chest showing the formation of an atriotomy according to the method of the invention.

With an opening formed in the pericardium, the right lateral wall of the left atrium is in a direct line of sight from the right lateral chest looking through inner lumen 338 of oval port 334. An atriotomy incision AI is then made in the left atrial wall W by means of thoracoscopic scissors 362 and graspers 364 introduced through instrument ports 336 and/or through oval port 334, as illustrated in FIG. 38. Atriotomy AI is located between and just anterior to the pulmonary veins PV.

Before making atriotomy incision AI, it may be advantageous to flood the thorax with cool carbon dioxide ($CO_2$)

and to maintain this $CO_2$ blanket around the heart throughout the procedure in order to help exclude air from the chest cavity and heart, thereby reducing the risk of trapped air embolism in the heart. In such cases, retraction port 332, oval port 334 and instrument ports 336 may include gaseous seals like those used in laparoscopic trocar sleeves to prevent loss of $CO_2$ from the chest cavity and/or introduction of air into the chest cavity. $CO_2$ may be introduced through an insufflation tube introduced through one of these ports, or through an insufflation lumen extending through one of the ports.

Figure 39:
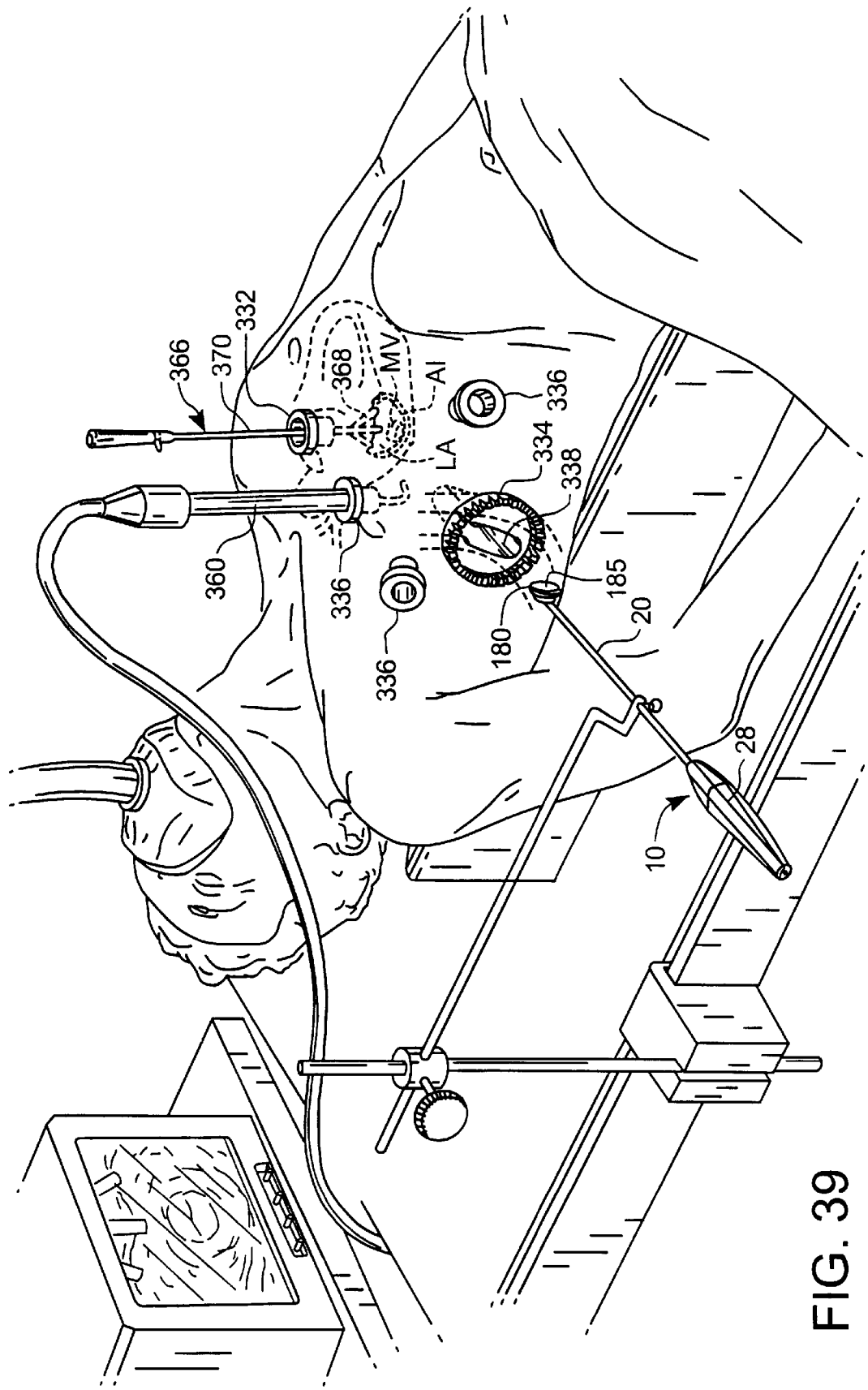
FIG. 39 is a perspective view of a patient illustrating the refraction of the atriotomy and positioning of a valve sizing according to the method of the invention.
Figure 40:
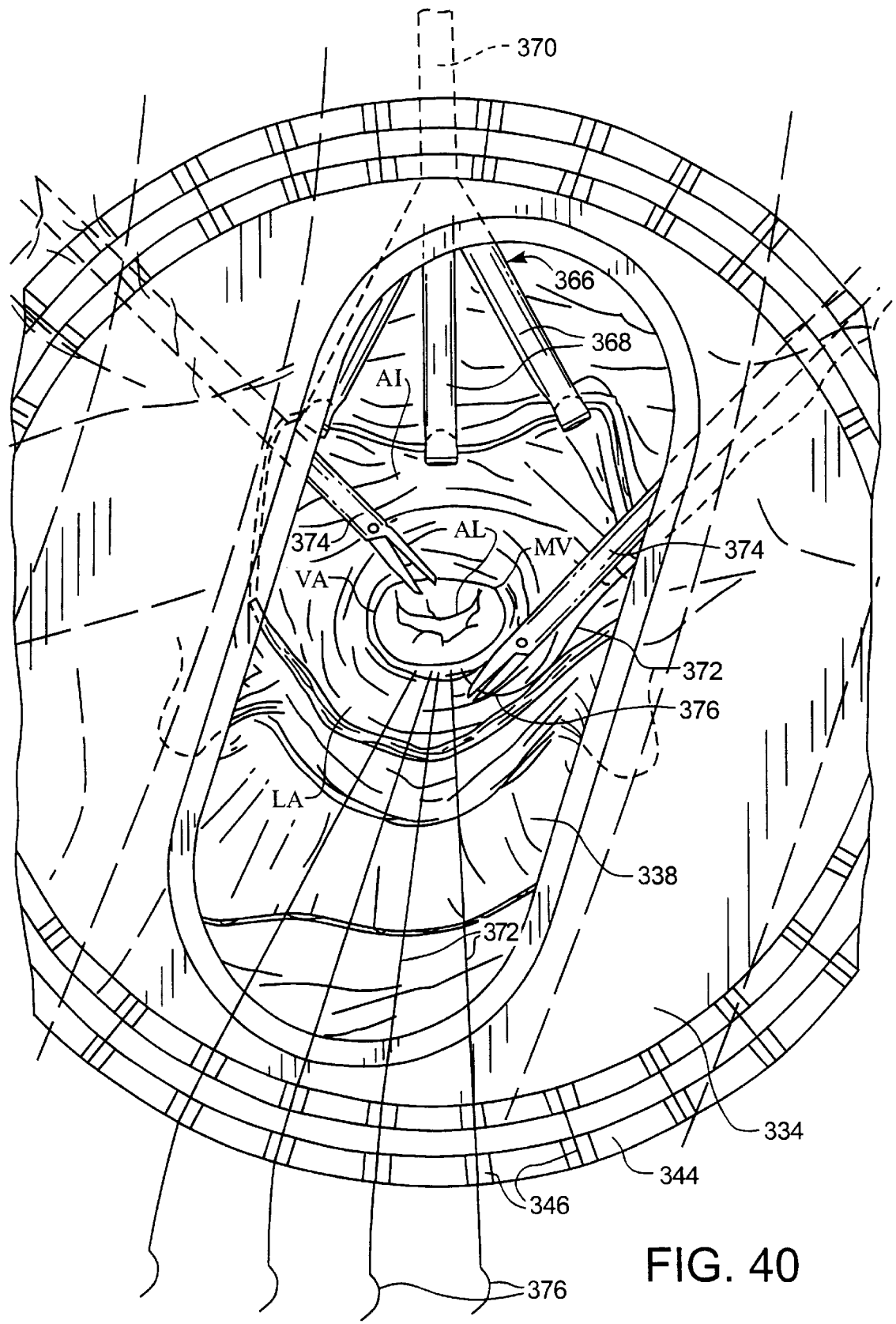
FIG. 40 is an elevational view through the oval port of FIGS. 36A–36D positioned in a right lateral location of a patient's chest showing the placement of sutures near the mitral valve according to the method of the invention.

Referring to FIGS. 39–40, an endoscopic atrial retractor 366 is then inserted through retraction port 332, positioned in atriotomy AI, and pulled anteriorly so as to retract atriotomy AI open. A rake-type retractor with several collapsible blades 368 (best seen in FIG. 40), coupled to the end of an elongated handle 370 may be used for this purpose, as described in copending application Ser. No. 08/281,962, filed Jul. 28, 1994. Alternatively, a retractor having a single larger transverse blade which is attachable and removable from an elongated handle may be used, as described in copending application Ser. No. 08/294,454, filed Aug. 23, 1994, which is incorporated herein by reference. The single blade may be introduced through inner lumen 338 of oval port 334 while the handle is introduced through retraction port 332, the blade then being attached to the handle within the chest cavity, and positioned within atriotomy AI to facilitate retraction. With atriotomy AI retracted, direct visualization of mitral valve MV is possible through inner lumen 338 of oval port 334, as shown in FIG. 40.

Under either direct visualization through a port or video-based viewing using thoracoscope 360, the condition of mitral valve MV is then assessed to determine whether the valve may be repaired, or whether replacement of the valve is necessary. If the surgeon determines that repair is the more suitable option, a number of repair procedures may be performed, including annuloplasty, wherein an annuloplasty ring is attached around the native valve to contract the annulus, quadrangular resection, in which a portion of a valve leaflet is excised and the remaining portions of the leaflet are sewn back together, commissurotomy, wherein the valve commissures are incised to separate the valve leaflets, shortening of the chordae tendonae, reattachment of severed chordae tendonae or papillary muscle tissue, and decalcification of the valve leaflets or annulus. Several of these procedures may also be performed on the same valve. In particular, annuloplasty rings may be used in conjunction with any repair procedures where contracting or stabilizing the valve annulus might be desirable.

In a preferred method of annuloplasty according to the invention, a prosthetic annuloplasty ring is introduced through oval port 334 and attached to an interior wall of the heart around the native valve annulus VA of mitral valve MV. In order to select an annuloplasty ring of the proper size, the native valve must be measured using a sizing device such as sizing disk 180 or 194 described above in connection with FIGS. 21–22. As illustrated in FIG. 39, sizing disk 180 is attached to coupling member 26 on the distal end of delivery handle 10, and pivoted relative to shaft 20 into an orientation appropriate for introduction through inner lumen 338 of oval port 334. Preferably, in this orientation, the lower face 185 of sizing disk 180 will be generally parallel to the longitudinal axis of shaft 20. Sizing disk 180 is then introduced through oval port 334 and through atriotomy AI using delivery handle 10, until the sizing disk is within the left atrium LA. Sizing disk 180 is then pivoted using actuator button 30 on handle 28 such that lower face 185 is facing mitral valve MV, approximately perpendicular to the longitudinal axis of shaft 20. Under visualization with thoracoscope 360 and/or direct vision through a port, sizing disk 180 is positioned adjacent or against mitral valve MV and the size of the native valve is measured, usually by measuring the width of the anterior leaflet AL (FIG. 40) by comparing the width of sizing disk 180, and by measuring the spacing between the native valve commissures or trigones using notches 184 or other markings on sizing disk 180. Sizing disks of various sizes may be interchanged on delivery handle 10 and positioned adjacent mitral valve MV until the proper size has been determined.

With an annuloplasty ring of the appropriate size identified, sutures are placed in or just outside of the native valve annulus VA, as illustrated in FIG. 40. Double-armed sutures 372 of braided polyester or Nylon and having a length of about 30–36 cm are preferred. Thoracoscopic needle drivers 374 may be used to grasp a curved suture needle 376 on one end of a suture 372, position the suture in left atrium LA through oval port 334 or an instrument port 336, and drive needle 374 through valve annulus VA in the manner shown in FIG. 40. Appropriate thoracoscopic needle drivers are described in copending application Ser. Nos. 08/281,962, filed Jul. 28, 1994, and Ser. No. 08/194, 946, filed Feb. 11, 1994, which have been incorporated herein by reference. Suture placement is visualized either by direct vision through oval port 334 or by using thoracoscope 360. Usually between 8 and 20 double-armed sutures 372 are placed in valve annulus VA. After being placed, suture needles 376 are drawn out of the chest cavity through inner lumen 338 of oval port 334, and sutures 372 are inserted into slots 346 in organizing ring 344.

Figure 41:
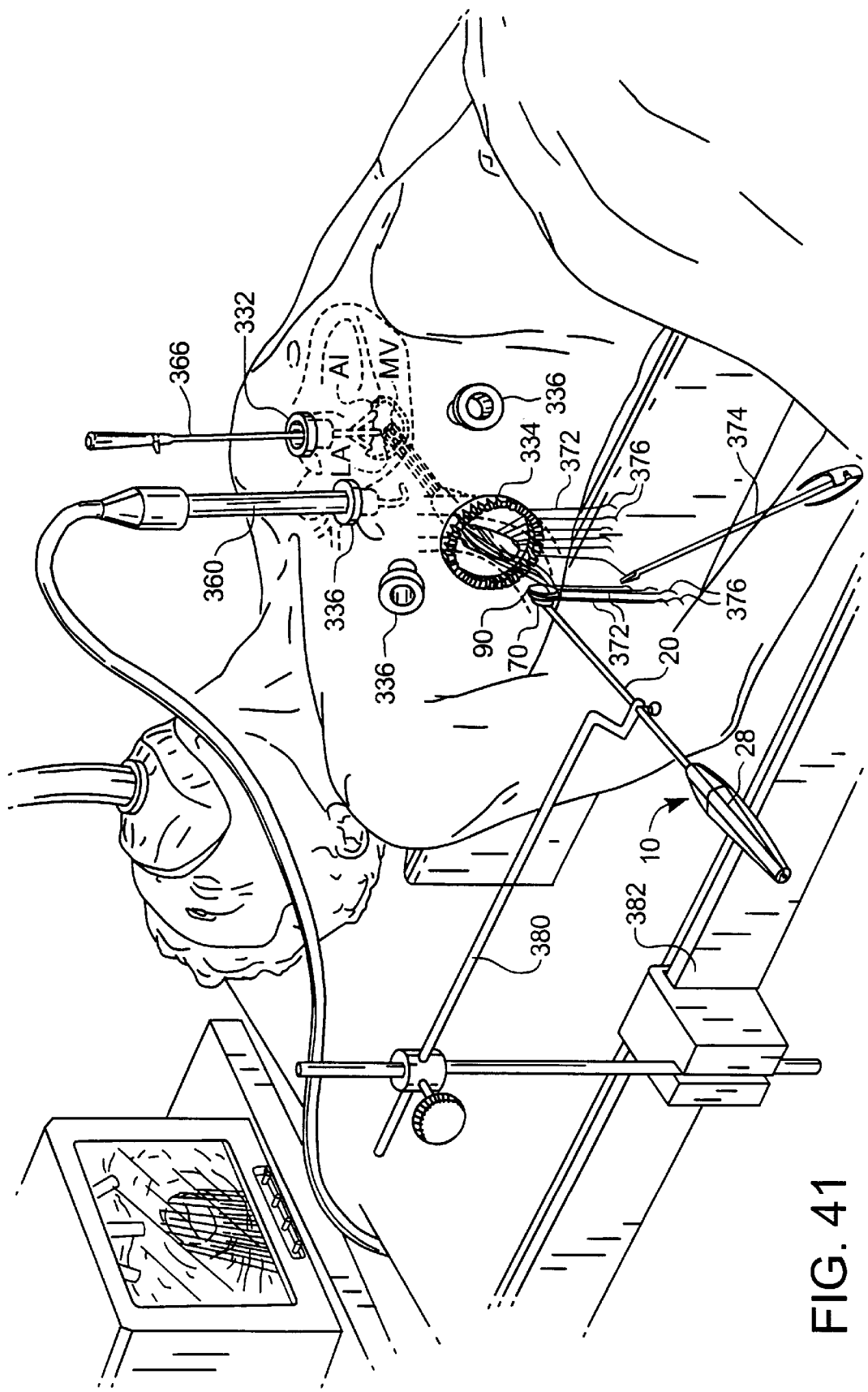
FIG. 41 is a perspective view of a patient illustrating the placement of sutures through the annuloplasty ring according to the method of the invention.

Sutures 372 are next placed through annuloplasty ring 90 on holder 70, as illustrated in FIG. 41. Holder 70 is attached to holder coupling 26 on delivery handle 10, which optionally may be held in a clamping fixture 380 attached to the operating table 382. Each suture needle 376 is grasped in a needle driver 374 and passed through annuloplasty ring 90. Sutures 372 may then be placed in a suture organizer, or a pair of hemostats (not shown) may be clamped onto each needle 376 and suspended from annuloplasty ring 90 to maintain tension on the sutures and prevent tangling.

Figure 42:
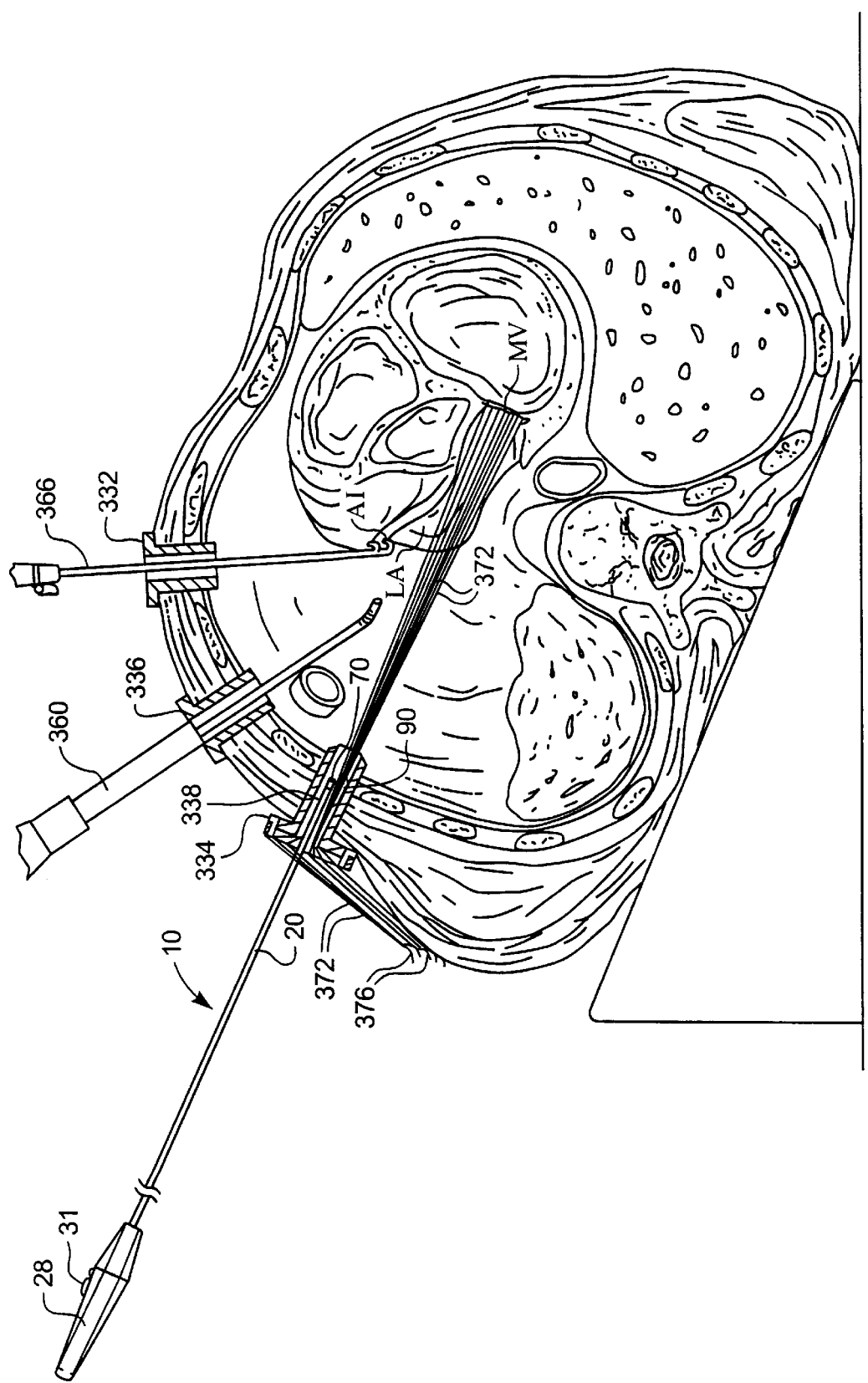
FIG. 42 is a transverse cross-section of a patient's thorax showing the introduction of the annuloplasty ring through an intercostal port according to the method of the invention.

Annuloplasty ring 90 is then introduced through inner lumen 338 of oval port 334, as illustrated in FIG. 42. Holder 70 is pivoted relative to shaft 20 so that annuloplasty ring 90 will pass through inner lumen 338 without interference, preferably in an orientation in which a plane containing the lower surface of annuloplasty ring 90 is parallel to the longitudinal axis of shaft 20. As annuloplasty ring 90 is advanced into the left atrium LA, tension is maintained on sutures 372 by organizer ring 344 or by individual hemostats (not pictured) clamped onto each pair of needles 376 on sutures 372 so that the annuloplasty ring slides along the sutures up to the mitral valve MV. Once through oval port 334 and into the chest cavity, actuator button 30 on delivery handle 10 may be actuated so that annuloplasty ring 90 pivots into an orientation suitable for attachment within the left atrium LA, preferably in an orientation in which the lower surface of the annuloplasty ring is parallel to the mitral valve and perpendicular to the longitudinal axis of shaft 20. Annuloplasty ring 90 is positioned in contact with the interior wall of the left atrium in which sutures 372 have been placed so as to surround the native valve annulus VA.

Holder 70 may then be removed from annuloplasty ring 90 by cutting any sutures used to retain ring 90 on the holder, and urging ring 90 out of channel 76 on the side of holder 70. Holder 70 and delivery handle 10 may then be removed from the chest cavity.

Figure 43:
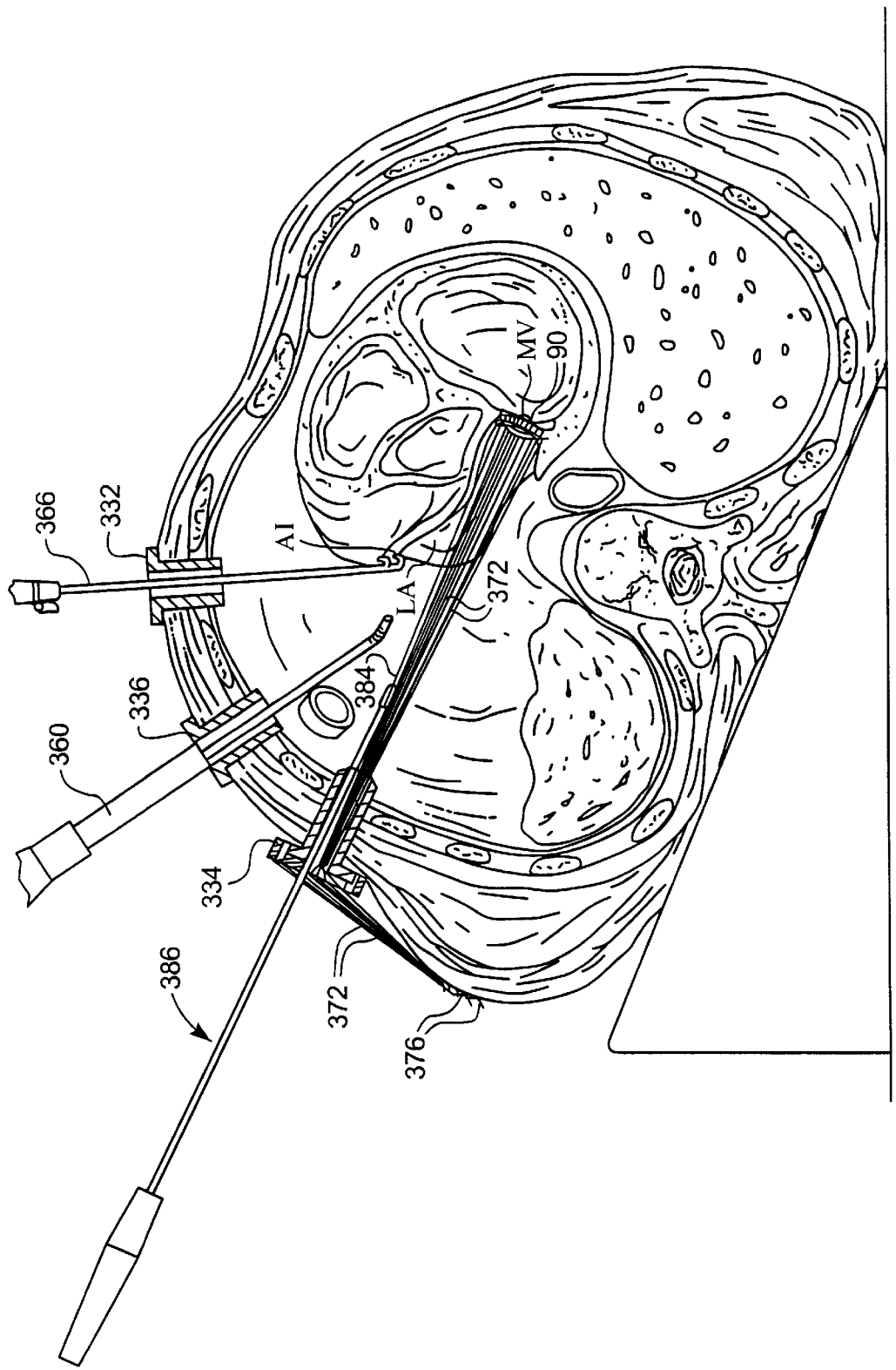
FIG. 43 is a transverse cross-section of a patient's thorax showing the pushing of suture knots through an intercostal port for securing the annuloplasty ring within the heart according to the method of the invention.
Figure 44:
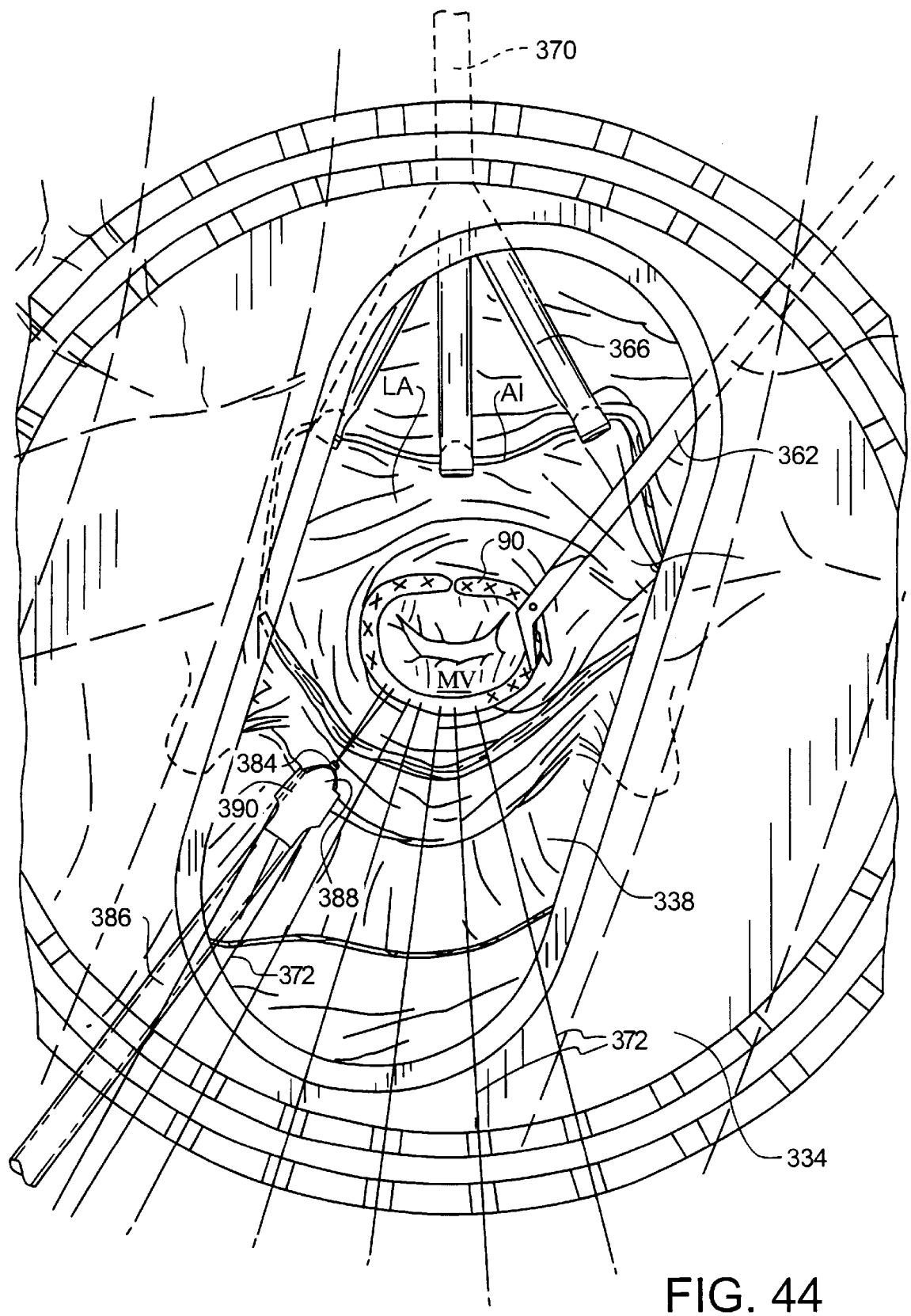
FIG. 44 is an elevational view through the oval port of FIGS. 36A–36D positioned in a right lateral location of a patient's chest showing the pushing of suture knots against the annuloplasty ring and trimming the ends of the sutures according to the method of the invention.
Figure 45:
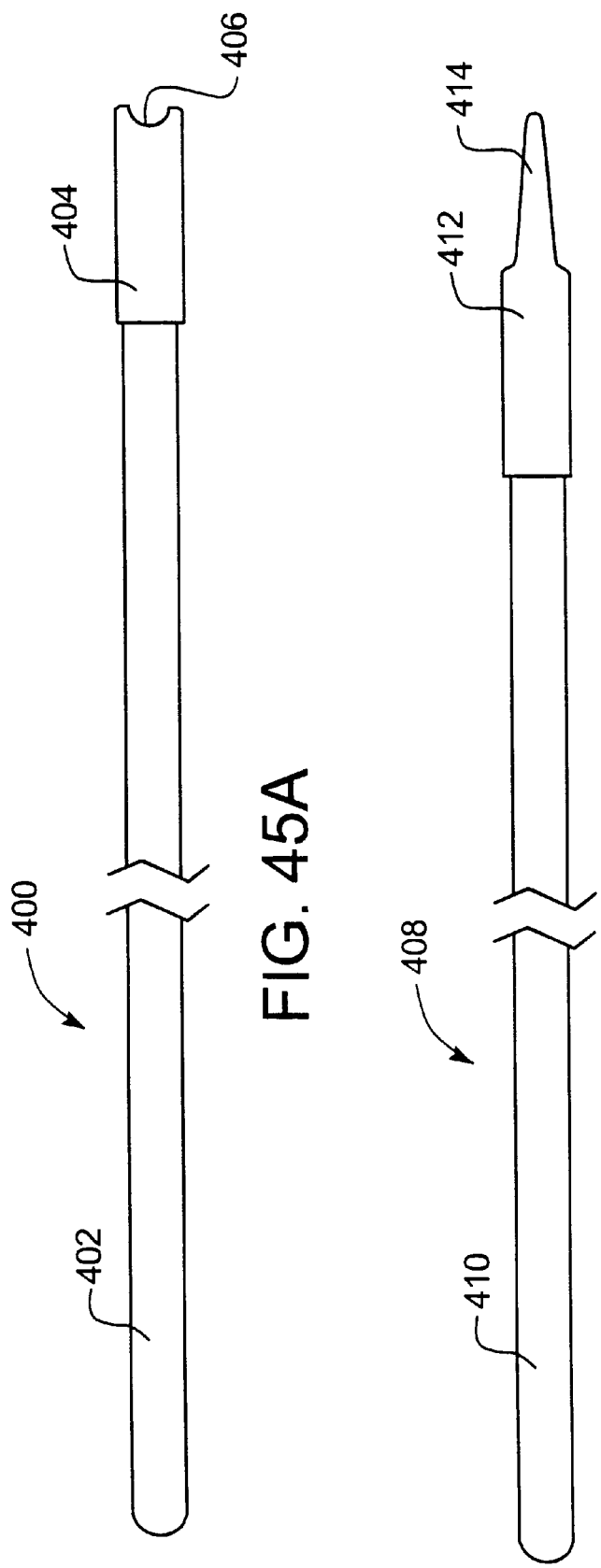
FIGS. 45A–45B are side elevational views of a valve seating device and a leaflet testing device, respectively, constructed in accordance with the principles of the invention.

Needles 376 are then trimmed from each suture 372, and, as illustrated in FIGS. 43–44, knots 384 are tied in each suture 372 and pushed into left atrium LA and against annuloplasty ring 90 by an endoscopic knot pusher 386. Knot pusher 386 preferably comprises a knot pusher with a rounded distal end 388 and a single lateral eyelet 390, as disclosed in copending application Ser. No. 08/288,674, filed Aug. 10, 1994, which is incorporated herein by reference. This knot pusher is particularly well-adapted for the method of the invention due its long length and low profile, and due to the quickness with which knots can be tied and the ease with which they can be slid into the left atrium from outside of the chest cavity. After each suture 372 is tied securely against annuloplasty ring 90, the suture ends are trimmed off using thoracoscopic scissors 362.

If neither annuloplasty nor any other repair procedure will adequately treat the diseased valve, the surgeon may elect to replace the native valve with a replacement valve. The techniques for introducing and securing a replacement valve within the heart will be analogous to those described above for annuloplasty ring 90, and are further described in copending application Ser No. 08/281,962, filed Jul. 28, 1994, which has been incorporated herein by reference. The native valve may be sized for replacement using valve sizing disks 220 or 238, shown in FIGS. 23–25, which are introduced into left atrium LA using delivery handle 10 by techniques similar to those described above for sizing mitral valve MV for an annuloplasty ring. Once a prosthetic valve 262 of the appropriate size is identified, thoracoscopic needle drivers 274 may be used to place sutures around the native valve annulus, in much the same way as described above for annuloplasty ring 90, using a mattress stitch or everted mattress stitch. As in the case of annuloplasty, the sutures are withdrawn from the body cavity through inner lumen 338 of oval port 334 and placed in slots 346 of organizing ring 344. Each suture is then placed through sewing ring 266 of prosthetic valve 262 outside of the chest cavity. Optionally, prior to suture placement, the valve leaflets of the native valve may be removed using thoracoscopic scissors 362.

Prosthetic valve 262, held on valve holder 260 (described above in connection with FIGS. 26–34), is then attached to delivery handle 10 to facilitate delivery of the replacement valve through oval port 334 into left atrium LA. During introduction, prosthetic valve 262 is pivoted into an orientation in which it will pass through inner lumen 338 of oval port 334 without interference, preferably with the longitudinal axis of sewing ring 266 approximately perpendicular to the longitudinal axis of shaft 20 as shown in FIG. 30A. Once within the chest cavity, prosthetic valve 262 is pivoted into an orientation suitable for attachment at the native valve position in the heart, preferably with the longitudinal axis of sewing ring 266 perpendicular to the interior wall of the heart to which the valve will be attached, and parallel to the longitudinal axis of shaft 20 as shown in FIG. 30B. Prosthetic valve 262 may then be removed from holder 260 by cutting retaining suture 300, and holder 260 and delivery handle 10 are removed from the chest cavity.

It may be necessary to seat the prosthetic valve firmly against the native valve annulus after holder 260 and delivery handle 10 have been removed. A valve seater 400, illustrated in FIG. 45A, may be utilized for this purpose. Valve seater 400 comprises an elongated rigid shaft 402, and a valve engaging tip 404 at its distal end. Valve engaging tip 404 has a concave end 406 radiused so as to match sewing ring 266, and is made of a soft polymer such as silicone rubber or thermoplastic elastomer (TPE) with a durometer in a range of 20 to 70 Shore A so that it can contact the prosthetic valve without damaging it. Valve seater 400 has a length of at least about 20 cm and usually at least 30 cm so as to reach the mitral position from outside the chest cavity via an intercostal port, and a diameter of less than about 25 mm, usually less than about 8 mm, so as to be positionable through an intercostal port. In this way, valve seater 400 may be positioned through an intercostal port (e.g. oval port 334) and tip 404 can be used to push against sewing ring 266 to seat the prosthetic valve against the native valve annulus.

Knots are then formed in the sutures and pushed into the left atrium using thoracoscopic knot pusher 386. The sutures are then trimmed off above the knot using thoracoscopic scissors 362, as described above.

Before or after the prosthetic valve has been secured in the heart, it may be necessary to test its leaflets to ensure they are functioning properly. A leaflet testing device as illustrated in FIG. 45B may be used for this purpose. Leaflet testing device 408 comprises a rigid shaft 410 and a leaflet-engaging tip 412 attached to the distal end of shaft 410. Shaft 410 has a length of at least about 20 cm usually at least 30 cm, and a diameter of less than about 25 mm, usually less than about 8 mm, to reach the mitral position from outside the chest via a right lateral intercostal port. Tip 412 has a tapered distal end 414 configured to push lightly on each valve leaflet 270 (FIG. 28) to fully open the leaflet without interference with annular frame 264. Because valve leaflets 270 may be fragile and susceptible to damage, tip 412 is made of a soft polymer such as silicone rubber or thermoplastic elastomer (TPE) with a durometer in a range of 20 to 70 Shore A. In this way, leaflet testing device 408 may be introduced through oval port 334 and each leaflet of the valve prosthesis pushed gently distally to ensure the leaflets are opening properly.

For certain types of heart valves prostheses, it may also be desirable to rotate the annular frame and valve leaflets relative to the sewing ring after the prosthesis has been secured in the heart. For this purpose, a specially designed valve rotator may be used. The valve rotator has an atraumatic rotator head for engaging the valve frame and/or leaflets similar to that disclosed in U.S. Pat. No. 5,403,305, which is incorporated herein by reference. However, rather than a socket which connects the head to a handle such that the face of the head is perpendicular to the handle, the rotator head used in the method of the present invention has a handle coupling like handle coupling 80 of FIGS. 5A–5C. In this way the rotator head may be connected to holder coupling 26 of delivery handle 10 so that it may be positioned in an edge-first orientation for introduction through an intercostal port, then pivoted into a face-first orientation for rotating the valve prosthesis.

Figure 46:
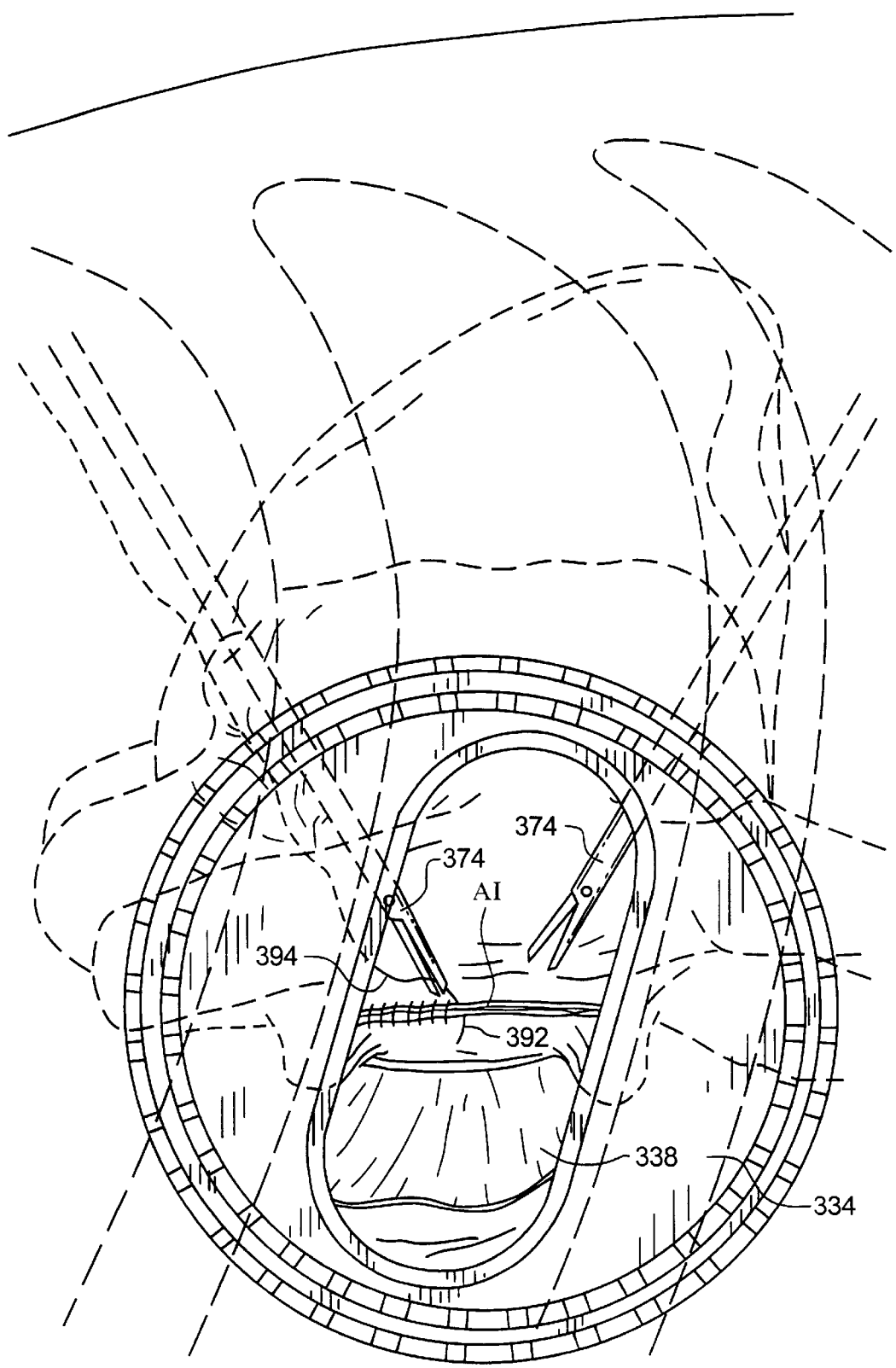
FIG. 46 is an elevational view through the oval port of FIGS. 36A–36D positioned in a right lateral location of a patient's chest showing the closure of the atriotomy according to the method of the invention.

When annuloplasty ring 90 or replacement valve 262 has been secured within the heart, atriotomy AI may be closed, as illustrated in FIG. 46. Thoracoscopic needle drivers 374 may be used to grasp a curved needle 392 on a suture 394, introduce suture 394 into the chest cavity through oval port 334 or an instrument port 336, and drive needle 392 through the left atrial wall to create a series of stitches across atriotomy AI. Alternatively, an endoscopic stapling device such as an AutoSuture™ Powered Multifire Endo TA60, available from United States Surgical Corp. of Norwalk, Conn., or an endoscopic fascia stapler, may be inserted through an anterior instrument port 336 and positioned around atriotomy AI to drive a series of staples into the atrial wall to close the atriotomy.

The opening formed in the pericardium may be closed with sutures or staples in a manner similar to that used for closing atriotomy AI. However, in most cases, closure of the pericardium is not necessary, and the opening may be left in it without adverse effect.

To complete the operation, cardiac function is restored by discontinuing delivery of cardioplegic fluid, terminating occlusion of the ascending aortic lumen, and perfusing the myocardium with warm blood. Preferably, where an aortic catheter has been used for aortic occlusion and cardioplegic fluid delivery, the expandable member on the distal end of the aortic catheter is deflated and warm blood is allowed to flow into the coronary arteries. If sinus rhythm is does not return immediately, electrical defibrillation may be used to stimulate the heart and/or pacing leads may be placed through a port into the heart muscle to pace the heart for a period of time postoperatively. Once the heart is beating normally, the aortic catheter may be removed from the patient, along with any venting catheter or retrograde cardioplegia delivery catheter which may have been used. Chest tubes may be inserted into the chest to provide drainage. The patient is then weaned from cardiopulmonary bypass, and the arterial and venous cannulae are removed from the patient. All venous and arterial punctures or cutdowns are closed. Any endotracheal tubes used for ventilation are removed. Retraction port 332, oval port 334, and instrument ports 336 are removed from the chest, and all intercostal incisions and punctures are closed. The patient is then recovered from anesthesia.

It will be understood to those of ordinary skill in the art that, while the invention has been described specifically in the context of mitral valve repair and replacement, the devices and methods disclosed herein will have equal application to a number of other cardiac valves, including the aortic valve, the tricuspid valve, and the pulmonary valve. While the specific locations of these valves and the surgical approaches utilized to access these valves may differ from those described in detail above, the devices and methods described herein are easily adapted for use on valves other than the mitral without departing from the scope of the invention. For example, the tricuspid or pulmonary valves may be accessed similarly to the mitral valve through an intercostal port in the right lateral chest to access the right atrium (for the tricuspid valve) or the right ventricle (for the pulmonary valve), on the other hand, the aortic valve can be accessed from an intercostal port in the upper anterior chest via an incision in the ascending aorta. Moreover, although the devices and methods of the invention have been described in connection with specific types of prosthetic annuloplasty rings and replacement valves, these are given by way of example only. It should be understood that a wide variety of prostheses may be implanted using the devices and methods of the invention with little if any modification to the specific embodiments described above.

Using the devices and methods of the invention, a cardiac valve may be repaired or replaced using minimally-invasive techniques which eliminate the need for a median sternotomy or other gross thoracotomy involving cutting, removal, or substantial retraction of the ribs or sternum. As a result, patient recovery is accelerated, pain and trauma are greatly reduced, and the morbidity and mortality of valve repair and replacement procedures may be decreased. Not only may this result in better outcomes and reduced costs for the thousands of patients who undergo cardiac valve surgery each year, but may allow thousands more suffering from valve disease to receive surgical treatment who would otherwise be unable or unwilling to tolerate the pain and trauma of open-heart valve surgery.

While the above is a complete description of the preferred embodiments of the invention, various alternatives, modifications, additions, and substitutions are possible without departing from the scope thereof. Therefore, the above should not be taken as limiting the scope of the invention, which is defined by the following claims.

What is claimed is:

1. A system for repairing a heart valve in a patient's heart, the system comprising:

an annuloplasty device configured for attachment within the heart around the heart valve, the annuloplasty device having an attachment portion configured to be attached to a patient's heart, the attachment portion generally defining a plane;

a device holder configured to be releasably coupled to the annuloplasty device, the device holder having a curved outer edge and the annuloplasty device being mounted to the curved outer edge; and an elongated handle for delivering the device holder and the annuloplasty device through an opening in a patient's chest, the handle being attached to the device holder such that the handle, the device holder, and the annuloplasty device together have a profile with a profile height of less than 30 mm, the profile height being in a direction perpendicular to the plane defined by the attachment portion.

2. The system of claim 1 further comprising a retractor sized and configured to retract tissue around the opening in the patient to facilitate positioning the annuloplasty device therethrough.

3. The system of claim 2 wherein the retractor includes a cannula having a distal end positionable in the chest cavity through an intercostal space, a proximal end, and an inner lumen through which the annuloplasty device and the device holder may be positioned while attached to the handle.

4. The system of claim 3 wherein the inner lumen of the cannula has a cross-sectional height and a cross-sectional width, the cross-sectional height being larger than the cross-sectional width.

5. The system of claim 4 wherein the annuloplasty device has a device width in a direction perpendicular to the profile height, the cross-sectional height of the inner lumen being larger than the device width, and the cross-sectional width of the inner lumen being larger than the profile height.

6. The system of claim 5 wherein the cross-sectional height is at least about 1.5 times the cross-sectional width.

7. The system of claim 4 wherein the inner lumen has a shape selected from oval, rectangular, and trapezoidal.

8. The system of claim 3 further comprising an obturator removably positionable in the inner lumen to facilitate introduction of the cannula through the opening.

9. The system of claim 2 further comprising a suture organizer having a number of suture holders configured to retain a plurality of sutures in positions outside the patient's chest cavity.

10. A system for repairing a heart valve in a patient's heart, the system comprising:

an annuloplasty device configured for attachment within the heart around the heart valve, the annuloplasty device having an attachment portion configured to be attached to a patient's heart, the attachment portion generally defining a plane;

a device holder releasably coupled to the annuloplasty device;

an elongated handle for delivering the device holder and the annuloplasty device through an opening in a patient's chest, the handle being attached to the device holder such that the handle, the device holder, and the annuloplasty device together have a profile with a profile height of less than 30 mm, the profile height being in a direction perpendicular to the plane defined by the attachment portion;

a retractor sized and configured to retract tissue around the opening in the patient to facilitate positioning the annuloplasty device therethrough; and a suture organizer having a number of suture holders configured to retain a plurality of sutures in positions outside the patient's chest cavity;

the suture organizer being attached to the retractor.

11. A system for repairing a heart valve in a patient's heart, the system comprising:

an annuloplasty device configured for attachment within the heart around the heart valve, the annuloplasty device having an attachment portion configured to be attached to a patient's heart, the attachment portion generally defining a plane;

a device holder releasably coupled to the annuloplasty device;

an elongated handle for delivering the device holder and the annuloplasty device through an opening in a patient's chest, the handle being attached to the device holder such that the handle, the device holder, and the annuloplasty device together have a profile with a profile height of less than 30 mm, the profile height being in a direction perpendicular to the plane defined by the attachment portion;

a retractor sized and configured to retract tissue around the opening in the patient to facilitate positioning the annuloplasty device therethrough; and a suture organizer having a number of suture holders configured to retain a plurality of sutures in positions outside the patient's chest cavity;

the retractor including a cannula having a distal end positionable in the chest cavity through the intercostal space, a proximal end, and an inner lumen, and the suture holders each include a slot disposed in a proximal end of the cannula around the inner lumen.

12. The system of claim 1 wherein the handle has a length of at least about 20 cm.

13. The method of claim 12 wherein the second vascular graft is selected from the group including a left internal mammary artery, a right internal mammary artery, a gastroepiploic artery, a radial artery, an inferior epigastric artery, a splenic artery, a saphenous vein, and a prosthetic vascular graft.

14. The system of claim 1 wherein the handle has a longitudinal axis which is at an angle of about 0°+/−45° relative to the plane.

15. The system of claim 1 wherein the device holder is pivotably coupled to the handle.

16. The system of claim 15 wherein the device holder is pivotable relative to the handle between a first position and a second position, the handle having a longitudinal axis which forms an angle of 0°+/−45° relative to the plane when in the first position, the longitudinal axis of the handle forming an angle of 90°+/−20° relative to the plane when in the second position.

17. The system of claim 15 wherein the handle further comprises an actuator at a proximal end thereof for pivoting the device holder.

18. The system of claim 1 wherein the device holder includes means for retaining the annuloplasty device on the device holder.

19. The system of claim 18 wherein the retention means comprises at least one suture fastened to the device holder and extending around the annuloplasty device.

20. The system of claim 19 further comprising a groove or ridge on the device holder oriented transversely to the suture for guiding a cutting edge across the suture.

21. The system of claim 18 wherein the retention means comprises a flange around a lateral edge of the device holder.

22. The system of claim 21 wherein the retention means further comprises a retaining leaf movably coupled to the device holder, the retaining leaf being movable to a closed position in opposition to the flange to form a space therebetween for receiving the annuloplasty device.

23. The method of claim 21 wherein the heart is rotated about an axis disposed at an acute angle between 0 degrees and 90 degrees relative to a longitudinal axis extending from an aortic root toward an apex of the heart.

24. The system of claim 22 wherein the retaining leaf is pivotable about an axis perpendicular to a longitudinal axis of the annuloplasty device.

25. The system of claim 22 further comprising a catch for releasably locking the retaining leaf in the closed position.

26. A system for repairing a heart valve in a patient's heart, the system comprising:

an annuloplasty device configured for attachment within the heart around the heart valve, the annuloplasty device having an attachment portion configured to be attached to a patient's heart, the annuloplasty device generally defining a plane;

a device holder releasably coupled to the annuloplasty device; and an elongated handle for delivering the device holder and the annuloplasty device through an opening in a patient's chest, the handle having a proximal portion, a distal portion, and a longitudinal axis, the elongate handle being coupled to the device holder;

a pivoting mechanism disposed between the handle and annuloplasty device, the pivoting mechanism permitting pivotal movement of the annuloplasty device relative to the handle in a manner which changes an angle between the plane and the longitudinal axis.

27. The system of claim 26, further comprising:

a pivoting mechanism attached to the distal portion of the handle.

28. The system of claim 26, wherein:

the annuloplasty device being pivotable relative to the handle between a first position and a second position, the handle being substantially perpendicular to the plane in the first position and being substantially parallel to the plane in the second position.

29. The system of claim 26, wherein:

the annuloplasty device, handle and holder have a profile height of less than 30 mm when the annuloplasty device is in the second position, the profile height being measured in a direction perpendicular to the plane.

30. The system of claim 26, wherein:

the device holder has a recess extending in the direction of the plane, the recess having at least one opening;

the handle having a coupling extending into the recess.

* * * * *